(12) United States Patent
Baker et al.

(10) Patent No.: US 7,812,121 B2
(45) Date of Patent: Oct. 12, 2010

(54) GLP-2 MIMETIBODIES, POLYPEPTIDES, COMPOSITIONS, METHODS AND USES

(76) Inventors: Audrey E. Baker, 145 King of Prussia Rd., Radnor, PA (US) 19087; Beverly A. Moore, P.O. Box 776 Welsh & McKean Rd., Springhouse, PA (US) 19477; Thomas Nesspor, 145 King of Prussia Rd., Radnor, PA (US) 19087; Karyn O'Neil, 145 King Prussia Rd., Radnor, PA (US) 19087; Jeffrey M. Palmer, 1029 Hickory Ridge Dr., Chalfont, PA (US) 18914; Kristen Picha, 145 King of Prussia Rd., Radnor, PA (US) 19087; Sarah Sague, 145 King of Prussia Rd., Radnor, PA (US) 19087

( * ) Notice: Subject to any disclaimer, the term of this patent is extended or adjusted under 35 U.S.C. 154(b) by 425 days.

(21) Appl. No.: 11/848,635

(22) Filed: Aug. 31, 2007

(65) Prior Publication Data

US 2009/0117104 A1 May 7, 2009

Related U.S. Application Data

(60) Provisional application No. 60/824,160, filed on Aug. 31, 2006, provisional application No. 60/862,487, filed on Oct. 23, 2006.

(51) Int. Cl.
*A61K 38/16* (2006.01)
(52) U.S. Cl. .................. 530/324; 530/350; 530/387.3; 514/12
(58) Field of Classification Search .................. 530/324, 530/350, 387.3; 514/12
See application file for complete search history.

(56) References Cited

U.S. PATENT DOCUMENTS

| | | | | |
|---|---|---|---|---|
| 5,789,379 | A | * | 8/1998 | Drucker et al. ................ 514/12 |
| 7,112,567 | B2 | * | 9/2006 | Bridon et al. ................ 514/12 |
| 2001/0021767 | A1 | | 9/2001 | Drucker et al. |
| 2007/0036806 | A1 | | 2/2007 | Glaesner et al. |

FOREIGN PATENT DOCUMENTS

| | | |
|---|---|---|
| WO | WO 2005/097175 A2 | 10/2005 |
| WO | WO2007/067828 A2 | 6/2007 |

OTHER PUBLICATIONS

Hartmann, et al., "Structure, measurement and secretion of human glucagon-like peptide-2," Peptides, 21: 73-80 (2000).
Bjerknes, et al., "Modulation of specific intestinal epithelial progenitors by enteric neurons," Proceedings of the National Academy of Science USA, 92(22): 12497-12502 (2001).
Orskov, et al., "CLP-2 stimulates colonic growth via KGF, released subepithelial myofibroblasts with GLP-2 receptors," Science, 124: 105-112 (2004).
Bulut, et al., "Glucagon-like peptide 2 improves intestinal wound healing shown through induction of epithelial cell migration in vitro—evidence for a TFG-β-mediated effect," Regulatory Peptides, 121: 137-143 (2004).
Kalff, et al., "Biphasic response to gut manipulation and temporal correlation of cellular infiltrates and muscle dysfunction in rat," Surgery, 126: 498-509 (1999).
Wehner, et al., Induction of IL-6 within the rodent intestinal muscularis after intestinal surgical stress, Surgery, 137: 436-446 (2005).
Shibata, et al., "Effects of Prostaglandin $F_2\alpha$ and Cisapride on Small Intestinal Activity During the Early Postoperative Period in Humans," Surgery Today, 28: 787-791 (1998).
Viscusi, et al., "Alvimopan, a peripherally acting mu-opioid receptor antagonist, compared with placebo in postoperative ileus after major abdominal surgery," Surgery Endoscopy, 20: 64-70 (2006).
Platell, et al., "The management of patients with the short bowel syndrome," World Journal of Gastroenterology, 8(1): 13-20 (2002).
Holst, et al., "Glucagon-like Peptide 1 (GLP-1): An Intestinal Hormone, Signalling Nutritional Abundance, with an Unusual Therapeutic Potential," Trends in Endocrinology and Metabolism, 10(6): 229-235 (1999).
Anup, et al., "Surgical Stress and the Gastrointestinal Tract," Journal of Surgical Research, 92-291-300 (2000).
Bouras, et al., "Effect of cyclooxygenase-2 inhibitors on gastric emptying and small intestinal transmit in humans," Neurogastroenterology Motil., 16: 729-735 (2004).
Drucker, et al., "Induction of intestinal epithelial proliferation by glucagon-like peptide 2," Proceedings of the National Academy of Science USA, 93: 7911-7916 (1996).
Yusta, et al., "The Glucagon-like Peptide-2 Receptor Mediates Direct Inhibition of Cellular Apoptosis via A cAMP-dependent Protein Kinase-independent Pathway," The Journal of Biological Chemistry, 275(45): 35345-35352 (2000).
Hartmann, et al., "In Vivo and in Vitro Degradation of Glucagon-Like Peptide-2 in Humans," The Journal of Clinical Endocrinology & Metabolism, 85(8): 2884-2888 (2000).
Prasad, et al., "Glucagonlike Peptide-2 Analogue Enhances Intestinal Mucosal Mass After Ischemia and Reperfusion," Journal of Pediatric Surgery, 35(2): 357-259 (2000).
Josephs, et al., "Products of Cyclooxygenase-2 Catalysis Regulate Postoperative Bowel Motility," Journal of Surgical Research, 86: 50-54 (1999).
Brubaker, et al., "Minireview: Glucagon-Like Peptides Regulate Cell Proliferation and Apoptosis in the Pancreas, Gut, and Central Nervous System," Endocrinology, 145(6): 2653-2659 (2004).

(Continued)

*Primary Examiner*—Stephen L Rawlings
*Assistant Examiner*—Brad Duffy
(74) *Attorney, Agent, or Firm*—Kirk Baumeister

(57) ABSTRACT

Mammalian GLP-2 mimetibodies, polypeptides and nucleic acids are disclosed. Methods of utilizing the mimetibodies and polypeptides to treat GLP-2 related diseases are also disclosed.

10 Claims, 7 Drawing Sheets

OTHER PUBLICATIONS

Holte, et al., "Postoperative ileus: a preventable event," British Journal of Surgery, 97: 1480-1493 (2000).

Drucker, et al., "Glucagon-Like Peptide 2," The Journal of Clinical Endocrinology & Metabolism, 86(4): 1759-1764 (2001).

von Ritter, et al., "Neutrophilic Proteases: Mediators of Formyl-Methionyl-Leucyl-Phenylalanine-Induced Ileitis in Rats," Gastroenterology, 97: 605-609 (1989).

Troncone, et al., "Increased intestinal sugar permeability after challenge in children with cow's milk allergy or intolerance," Allergy, 49: 142-146 (1994).

H.B. Mikkelsen, "Macrophages in the external muscle layers of mammalian intestines," Histology and Histopathology, 10: 719-736 (1995).

Holte, et al., "Prevention of postoperative ileus," Minerva Anestesiology, 68: 152-156 (2002).

Kouris, et al., "The effect of glucagon-like peptide 2 on intestinal permeability and bacterial translocation in acute necrotizing pancreatitis," The American Journal of Surgery, 181: 571-575 (2001).

Holte, et al., "Postoperative ileus: a preventable event," British Journal of Surgery, 87: 1480-1493 (2000).

Gonenne, et al., "Effect of Alvimopan and codeine on Gastrointestinal Transit: A Randomized Controlled Study," Clinical Gastroenterology and Hepatology, 3: 784-791 (2005).

Shin, et al., "Glucagon-like peptide2: an update," Current Opinion in Endocrinology & Diabetes, 12(1): 63-71 (2005).

Bauer, et al., "Ileus in critical illness: mechanisms and management," Current Opinion in Critical Care, 8: 152-157 (2002).

Orskov, et al., "Carboxypeptidase-B-like processing of the C-terminus of glucagon-like peptide-2 in pig and human small intestine," FEB, 247(20): 193-196 (1989).

Jeppesen, et al., "Glucagon-like Peptide 2 Improves Nutrient Absorption and Nutritional Status in Short-Bowel Patients with No Colon," Gastroenterology, 120: 806-815 (2001).

Yusta, et al., "Enteroendocrine Localization of GLP-2 Receptor Expression in Humans and Rodents," Gastroenterology, 119: 744-755 (2000).

Kalff, et al., "Role of Inducible Nitric Oxide Synthase in Postoperative Intestinal Smooth Muscle Dysfunction in Rodents," Gastroenterology, 118: 316-327 (2000).

Schwarz, et al., "Prostanoid Production Via COX-2 as a Causative Mechanism of Rodent Postoperative Ileus," Gastroenterology, 121: 1354-1371 (2001).

Guan, et al., "GLP-2 Receptor Localizes to Enteric Neurons and Endocrine Cells Expressing Vasoactive Peptides and Mediates Increased Blood Flow," Gastroenterology, 130: 150-164 (2006).

Rubin, et al., "Nutrient Regulation of Intestinal Growth and Adaptation: Role of Glucagon-like Peptide 2 and the Enteroendocrine Cell," Gastroenterology, 117: 261-263 (1999).

Benjamin, et al., "Glucagon-like peptide 2 enhances intestinal epithelial barrier function of both transcellular and paracellular pathways in the mouse," Gut, 47(1): 112-119 (2000).

Kalff, et al., "Leukocytes of the intestinal muscularis: their phenotype and isolation," Journal of Leukocyte Biology, 63: 683-691 (1998).

Damholt, et al., "Proglucagon Processing Profile in Canine L Cells Expressing Endogenous Prohormone Convertase 1/3 and Prohormone convertase 2," Endocrinology, 140(10): 4800-4808 (1999).

Bielefedt, et al., "Intestinal Motility During Hypoxia and Reoxygenation in Vitro," Digestive Diseases & Sciences, 42(5): 878-884 (1997).

Kalff, et al., "Surgical Manipulation of the Gut Elicits an Intestinal Muscularis Inflammatory Response Resulting in Postsurgical Ileus," Annals of Surgery, 228(5): 652-663 (1998).

Turler, et al., "Colonic Postoperative Inflammatory Ileus in the Rat," Annals of Surgery, 236(10): 56-66 (2002).

Brubaker, et al., "Circulating and Tissue Forms of the Intestinal Growth Factor, Glucagon-Like Peptide-2," Endocrinology, 138(11): 4837-4843 (1997).

Kalff, et al., "Surgically Induced Leukocytic Infiltrates Within the Rate Intestinal Muscularis Mediate Postoperative Ileus," Gastroenterology, 117: 378-387 (1999).

Livingston, et al., "Postoperative Ileus," Digestive Diseases and Sciences, 35(1): 121-132 (1990).

Munroe, et al., "Prototypic G protein-coupled receptor for the intestinotrophic factor glucagon-like peptide 2," Proceedings of the National Academy of Science USA, 96: 1569-1573 (1999).

P.B. Jeppesen, "Clinical Significance of GLP-2 in Short-Bowel Syndrome," Journal of Nutrition, 133: 3721-3724 (2003).

Rothenberg, et al., "Evidence for Redundancy in Propeptide/Prohormone Convertase Activities in Processing Proglucagon: An Antisense Study," Molecular Endocrinology, 10: 331-341 (1996).

Oster, et al., "Hospitalization for 5-FU Toxicity in Metastatic Colorectal Cancer: Incidence and Cost," Oncology, 13: 41 (1999).

Stephen B. Hanauer, "Inflammatory Bowel Disease," New England Journal of Medicine, 334(13): 841-848 (1996).

J. Nightingale, "Short bowel, short answer?" Gut, 45: 478-479 (1999).

Boushey, et al., "Glucagon-like peptide 2 decreases mortality and reduces the severity of indomethacin-induced enteritis," American Journal of Physiology, 277: E937-E947 (1999).

Dhanvantari, et al., "Role of Prohormone Convertases in the Tissue-Specific Processing of Proglucagon," Molecular Endocrinology, 10: 342-355 (1996).

* cited by examiner

SEQUENCE LISTING

```
<160> NUMBER OF SEQ ID NOS: 80

<210> SEQ ID NO 1
<211> LENGTH: 33
<212> TYPE: PRT
<213> ORGANISM: Homo sapiens

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 2
```

```
<211> LENGTH: 33
<212> TYPE: PRT
<213> ORGANISM: Artificial Sequence
<220> FEATURE:
<223> OTHER INFORMATION: GLP-2 variant

<400> SEQUENCE: 2

His Ser Asp Gly Ser Phe Ser Asp Glu Met Asn Thr Ile Leu Asp Asn
 1               5                  10                  15

Leu Ala Ala Arg Asp Phe Ile Asn Trp Leu Ile Gln Thr Lys Ile Thr
             20                  25                  30

Asp

<210> SEQ ID NO 3
<211> LENGTH: 33
<212> TYPE: PRT
<213> ORGANISM: Artificial Sequence
<220> FEATURE:
<223> OTHER INFORMATION: GLP-2 variant

<400> SEQUENCE: 3

His Gly Asp Gly Ser Phe Ser Asp Glu Met Asn Thr Ile Leu Asp Asn
 1               5                  10                  15

Leu Ala Ala Arg Asp Phe Ile Asn Trp Leu Ile Gln Thr Lys Ile Thr
             20                  25                  30

Asp

<210> SEQ ID NO 4
<211> LENGTH: 275
<212> TYPE: PRT
<213> ORGANISM: Artificial Sequence
<220> FEATURE:
<223> OTHER INFORMATION: Mimetibody

<400> SEQUENCE: 4

His Ser Asp Gly Ser Phe Ser Asp Glu Met Asn Thr Ile Leu Asp Asn
 1               5                  10                  15

Leu Ala Ala Arg Asp Phe Ile Asn Trp Leu Ile Gln Thr Lys Ile Thr
             20                  25                  30

Asp Gly Ser Gly Gly Gly Ser Gly Thr Leu Val Thr Val Ser Ser Glu
             35                  40                  45

Ser Lys Tyr Gly Pro Pro Cys Pro Pro Cys Pro Ala Pro Glu Ala Ala
         50                  55                  60

Gly Gly Pro Ser Val Phe Leu Phe Pro Pro Lys Pro Asp Thr Leu Met
65                  70                  75                  80

Ile Ser Arg Thr Pro Glu Val Thr Cys Val Val Val Asp Val Ser Gln
                 85                  90                  95

Glu Asp Pro Glu Val Gln Phe Asn Trp Tyr Val Asp Gly Val Glu Val
                100                 105                 110

His Asn Ala Lys Thr Lys Pro Arg Glu Glu Gln Phe Asn Ser Thr Tyr
            115                 120                 125

Arg Val Val Ser Val Leu Thr Val Leu His Gln Asp Trp Leu Asn Gly
        130                 135                 140

Lys Glu Tyr Lys Cys Lys Val Ser Asn Lys Gly Leu Pro Ser Ser Ile
145                 150                 155                 160

Glu Lys Thr Ile Ser Lys Ala Lys Gly Gln Pro Arg Glu Pro Gln Val
                165                 170                 175

Tyr Thr Leu Pro Pro Ser Gln Glu Glu Met Thr Lys Asn Gln Val Ser
            180                 185                 190
```

```
Leu Thr Cys Leu Val Lys Gly Phe Tyr Pro Ser Asp Ile Ala Val Glu
        195                 200                 205

Trp Glu Ser Asn Gly Gln Pro Glu Asn Asn Tyr Lys Thr Thr Pro Pro
    210                 215                 220

Val Leu Asp Ser Asp Gly Ser Phe Phe Leu Tyr Ser Arg Leu Thr Val
225                 230                 235                 240

Asp Lys Ser Arg Trp Gln Glu Gly Asn Val Phe Ser Cys Ser Val Met
                245                 250                 255

His Glu Ala Leu His Asn His Tyr Thr Gln Lys Ser Leu Ser Leu Ser
            260                 265                 270

Leu Gly Lys
        275

<210> SEQ ID NO 5
<211> LENGTH: 276
<212> TYPE: PRT
<213> ORGANISM: Artificial Sequence
<220> FEATURE:
<223> OTHER INFORMATION: Mimetibody

<400> SEQUENCE: 5

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Ser Gly Gly Ser Gly Thr Leu Val Thr Val Ser Ser Glu
            35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270
```

```
Ser Leu Gly Lys
        275

<210> SEQ ID NO 6
<211> LENGTH: 43
<212> TYPE: PRT
<213> ORGANISM: Artificial Sequence
<220> FEATURE:
<223> OTHER INFORMATION: Mimetibody

<400> SEQUENCE: 6

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Gly Ser Cys Pro Pro Cys Pro
        35                  40

<210> SEQ ID NO 7
<211> LENGTH: 48
<212> TYPE: PRT
<213> ORGANISM: Artificial Sequence
<220> FEATURE:
<223> OTHER INFORMATION: Mimetibody

<400> SEQUENCE: 7

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Gly Ser Gly Gly Gly Ser Cys Pro Pro Cys Pro
        35                  40                  45

<210> SEQ ID NO 8
<211> LENGTH: 53
<212> TYPE: PRT
<213> ORGANISM: Artificial Sequence
<220> FEATURE:
<223> OTHER INFORMATION: Mimetibody

<400> SEQUENCE: 8

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Gly Gly Gly Ser Gly Gly Gly Ser Gly Gly Gly Gly Ser
        35                  40                  45

Cys Pro Pro Cys Pro
        50

<210> SEQ ID NO 9
<211> LENGTH: 58
<212> TYPE: PRT
<213> ORGANISM: Artificial Sequence
<220> FEATURE:
<223> OTHER INFORMATION: Mimetibody

<400> SEQUENCE: 9

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30
```

Asp Gly Gly Gly Gly Ser Gly Gly Gly Ser Gly Gly Gly Ser
        35                  40                  45

Gly Gly Gly Gly Ser Cys Pro Pro Cys Pro
        50                  55

<210> SEQ ID NO 10
<211> LENGTH: 63
<212> TYPE: PRT
<213> ORGANISM: Artificial Sequence
<220> FEATURE:
<223> OTHER INFORMATION: Mimetibody

<400> SEQUENCE: 10

His Gly Asp Gly Ser Phe Ser Asp Glu Met Asn Thr Ile Leu Asp Asn
 1               5                  10                  15

Leu Ala Ala Arg Asp Phe Ile Asn Trp Leu Ile Gln Thr Lys Ile Thr
            20                  25                  30

Asp Gly Gly Gly Gly Ser Gly Gly Gly Ser Gly Gly Gly Ser
        35                  40                  45

Gly Gly Gly Gly Ser Gly Gly Gly Gly Ser Cys Pro Pro Cys Pro
        50                  55                  60

<210> SEQ ID NO 11
<211> LENGTH: 59
<212> TYPE: PRT
<213> ORGANISM: Artificial Sequence
<220> FEATURE:
<223> OTHER INFORMATION: Mimetibody

<400> SEQUENCE: 11

His Gly Asp Gly Ser Phe Ser Asp Glu Met Asn Thr Ile Leu Asp Asn
 1               5                  10                  15

Leu Ala Ala Arg Asp Phe Ile Asn Trp Leu Ile Gln Thr Lys Ile Thr
            20                  25                  30

Asp Gly Ser Gly Gly Gly Ser Gly Ala Leu Val Ala Val Ser Ser Glu
        35                  40                  45

Ser Lys Tyr Gly Pro Pro Cys Pro Pro Cys Pro
        50                  55

<210> SEQ ID NO 12
<211> LENGTH: 831
<212> TYPE: DNA
<213> ORGANISM: Artificial Sequence
<220> FEATURE:
<223> OTHER INFORMATION: Mimetibody

<400> SEQUENCE: 12
catggcgatg gttctttctc tgatgagatg aacaccattc ttgataatct tgccgctcga    60
gactttataa actggttgat tcagaccaaa atcactgacg gatccggtgg aggctccggt   120
accttagtca ccgtctcctc agagtccaaa tatggtcccc catgcccacc atgcccggcg   180
cctgaggccg ccggggggacc atcagtcttc ctgttccccc caaaacccaa ggacactctc   240
atgatctccc ggacccctga ggtcacgtgc gtggtggtgg acgtgagcca ggaagacccc   300
gaggtccagt tcaactggta cgtggatggc gtggaggtgc ataatgccaa gacaaagccg   360
cgggaggagc agttcaacag cacgtaccgt gtggtcagcg tcctcaccgt cctgcaccag   420
gactggctga acggcaagga gtacaagtgc aaggtctcca acaaaggcct cccgtcctcc   480
atcgagaaaa ccatctccaa agccaaaggg cagcctcgag agccacaggt gtacaccctg   540

| | |
|---|---|
| cccccatccc aggaggagat gaccaagaac caggtcagcc tgacctgcct ggtcaaaggc | 600 |
| ttctacccca gcgacatcgc cgtggagtgg gagagcaatg ggcagccgga gaacaactac | 660 |
| aagaccacgc ctcccgtgct ggactccgac ggctccttct tcctctacag caggctaacc | 720 |
| gtggacaaga gcaggtggca ggaggggaat gtcttctcat gctccgtgat gcatgaggct | 780 |
| ctgcacaacc actacacaca gaaaagcttg tccctgtctc tgggtaaatg a | 831 |

```
<210> SEQ ID NO 13
<211> LENGTH: 129
<212> TYPE: DNA
<213> ORGANISM: Artificial Sequence
<220> FEATURE:
<223> OTHER INFORMATION: Mimetibody

<400> SEQUENCE: 13
```

| | |
|---|---|
| catggcgatg gttctttctc tgatgagatg aacaccattc ttgataatct tgccgctcga | 60 |
| gactttataa actggttgat tcagaccaaa atcactgacg gaggaggtgg atcctgccca | 120 |
| ccatgcccg | 129 |

```
<210> SEQ ID NO 14
<211> LENGTH: 144
<212> TYPE: DNA
<213> ORGANISM: Artificial Sequence
<220> FEATURE:
<223> OTHER INFORMATION: Mimetibody

<400> SEQUENCE: 14
```

| | |
|---|---|
| catggcgatg gttctttctc tgatgagatg aacaccattc ttgataatct tgccgctcga | 60 |
| gactttataa actggttgat tcagaccaaa atcactgacg gaggaggtgg atccggtggt | 120 |
| ggcggcagtt gcccaccatg cccg | 144 |

```
<210> SEQ ID NO 15
<211> LENGTH: 159
<212> TYPE: DNA
<213> ORGANISM: Artificial Sequence
<220> FEATURE:
<223> OTHER INFORMATION: Mimetibody

<400> SEQUENCE: 15
```

| | |
|---|---|
| catggcgatg gttctttctc tgatgagatg aacaccattc ttgataatct tgccgctcga | 60 |
| gactttataa actggttgat tcagaccaaa atcactgacg gaggaggtgg atccggcggt | 120 |
| ggcggatctg gtggtggcgg cagttgccca ccatgcccg | 159 |

```
<210> SEQ ID NO 16
<211> LENGTH: 174
<212> TYPE: DNA
<213> ORGANISM: Artificial Sequence
<220> FEATURE:
<223> OTHER INFORMATION: Mimetibody

<400> SEQUENCE: 16
```

| | |
|---|---|
| catggcgatg gttctttctc tgatgagatg aacaccattc ttgataatct tgccgctcga | 60 |
| gactttataa actggttgat tcagaccaaa atcactgacg gaggaggtgg atccggtgga | 120 |
| ggaggctcag gcggtggcgg atctggtggt ggcggcagtt gcccaccatg cccg | 174 |

```
<210> SEQ ID NO 17
<211> LENGTH: 189
<212> TYPE: DNA
<213> ORGANISM: Artificial Sequence
```

```
<220> FEATURE:
<223> OTHER INFORMATION: Mimetibody

<400> SEQUENCE: 17
catggcgatg gttctttctc tgatgagatg aacaccattc ttgataatct tgccgctcga      60
gactttataa actggttgat tcagaccaaa atcactgacg gaggaggtgg atccggcgga     120
ggaggttccg gtggaggagg ctcaggcggt ggcggatctg gtggtggcgg cagttgccca     180
ccatgcccg                                                             189

<210> SEQ ID NO 18
<211> LENGTH: 177
<212> TYPE: DNA
<213> ORGANISM: Artificial Sequence
<220> FEATURE:
<223> OTHER INFORMATION: Mimetibody

<400> SEQUENCE: 18
catggcgatg gttctttctc tgatgagatg aacaccattc ttgataatct tgccgctcga      60
gactttataa actggttgat tcagaccaaa atcactgacg gatccggtgg aggctccggt     120
gccttagtcg ccgtctcctc agagtccaaa tatggtcccc catgcccacc atgcccg       177

<210> SEQ ID NO 19
<211> LENGTH: 4
<212> TYPE: PRT
<213> ORGANISM: Artificial Sequence
<220> FEATURE:
<223> OTHER INFORMATION: Linker

<400> SEQUENCE: 19

Gly Gly Gly Ser
 1

<210> SEQ ID NO 20
<211> LENGTH: 6
<212> TYPE: PRT
<213> ORGANISM: Artificial Sequence
<220> FEATURE:
<223> OTHER INFORMATION: Linker

<400> SEQUENCE: 20

Gly Ser Gly Gly Gly Ser
 1               5

<210> SEQ ID NO 21
<211> LENGTH: 8
<212> TYPE: PRT
<213> ORGANISM: Homo sapiens

<400> SEQUENCE: 21

Gly Thr Leu Val Thr Val Ser Ser
 1               5

<210> SEQ ID NO 22
<211> LENGTH: 8
<212> TYPE: PRT
<213> ORGANISM: Artificial Sequence
<220> FEATURE:
<223> OTHER INFORMATION: V2 variant

<400> SEQUENCE: 22

Gly Ala Leu Val Ala Val Ser Ser
 1               5
```

```
<210> SEQ ID NO 23
<211> LENGTH: 15
<212> TYPE: PRT
<213> ORGANISM: Homo sapiens

<400> SEQUENCE: 23

Glu Pro Lys Ser Cys Asp Lys Thr His Thr Cys Pro Pro Cys Pro
 1               5                  10                  15

<210> SEQ ID NO 24
<211> LENGTH: 15
<212> TYPE: PRT
<213> ORGANISM: Homo sapiens

<400> SEQUENCE: 24

Glu Pro Lys Ser Ala Asp Lys Thr His Thr Cys Pro Pro Cys Pro
 1               5                  10                  15

<210> SEQ ID NO 25
<211> LENGTH: 12
<212> TYPE: PRT
<213> ORGANISM: Homo sapiens

<400> SEQUENCE: 25

Glu Ser Lys Tyr Gly Pro Pro Cys Pro Ser Cys Pro
 1               5                  10

<210> SEQ ID NO 26
<211> LENGTH: 12
<212> TYPE: PRT
<213> ORGANISM: Homo sapiens

<400> SEQUENCE: 26

Glu Ser Lys Tyr Gly Pro Pro Cys Pro Pro Cys Pro
 1               5                  10

<210> SEQ ID NO 27
<211> LENGTH: 5
<212> TYPE: PRT
<213> ORGANISM: Homo sapiens

<400> SEQUENCE: 27

Cys Pro Pro Cys Pro
 1               5

<210> SEQ ID NO 28
<211> LENGTH: 110
<212> TYPE: PRT
<213> ORGANISM: Homo sapiens

<400> SEQUENCE: 28

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
```

-continued

```
                85                  90                  95

Ala Leu Pro Ala Pro Ile Glu Lys Thr Ile Ser Lys Ala Lys
            100                 105                 110

<210> SEQ ID NO 29
<211> LENGTH: 110
<212> TYPE: PRT
<213> ORGANISM: Homo sapiens

<400> SEQUENCE: 29

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 30
<211> LENGTH: 110
<212> TYPE: PRT
<213> ORGANISM: Homo sapiens

<400> SEQUENCE: 30

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 31
<211> LENGTH: 110
<212> TYPE: PRT
<213> ORGANISM: Homo sapiens

<400> SEQUENCE: 31

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45
```

```
Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys
            100                 105                 110

<210> SEQ ID NO 32
<211> LENGTH: 107
<212> TYPE: PRT
<213> ORGANISM: Homo sapiens

<400> SEQUENCE: 32

Gly Gln Pro Arg Glu Pro Gln Val Tyr Thr Leu Pro Pro Ser Arg Asp
 1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 33
<211> LENGTH: 107
<212> TYPE: PRT
<213> ORGANISM: Homo sapiens

<400> SEQUENCE: 33

Gly Gln Pro Arg Glu Pro Gln Val Tyr Thr Leu Pro Pro Ser Gln Glu
 1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Arg Leu Thr Val Asp Lys Ser Arg Trp Gln Glu Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 34
<211> LENGTH: 4
<212> TYPE: PRT
<213> ORGANISM: Homo sapiens

<400> SEQUENCE: 34
```

Cys Pro Ser Cys
1

<210> SEQ ID NO 35
<211> LENGTH: 553
<212> TYPE: PRT
<213> ORGANISM: Homo sapiens

<400> SEQUENCE: 35

Met Lys Leu Gly Ser Ser Arg Ala Gly Pro Gly Arg Gly Ser Ala Gly
1               5                   10                  15

Leu Leu Pro Gly Val His Glu Leu Pro Met Gly Ile Pro Ala Pro Trp
            20                  25                  30

Gly Thr Ser Pro Leu Ser Phe His Arg Lys Cys Ser Leu Trp Ala Pro
        35                  40                  45

Gly Arg Pro Phe Leu Thr Leu Val Leu Val Ser Ile Lys Gln Val
    50                  55                  60

Thr Gly Ser Leu Leu Glu Glu Thr Thr Arg Lys Trp Ala Gln Tyr Lys
65                  70                  75                  80

Gln Ala Cys Leu Arg Asp Leu Leu Lys Glu Pro Ser Gly Ile Phe Cys
                85                  90                  95

Asn Gly Thr Phe Asp Gln Tyr Val Cys Trp Pro His Ser Ser Pro Gly
            100                 105                 110

Asn Val Ser Val Pro Cys Pro Ser Tyr Leu Pro Trp Trp Ser Glu Glu
        115                 120                 125

Ser Ser Gly Arg Ala Tyr Arg His Cys Leu Ala Gln Gly Thr Trp Gln
    130                 135                 140

Thr Ile Glu Asn Ala Thr Asp Ile Trp Gln Asp Asp Ser Glu Cys Ser
145                 150                 155                 160

Glu Asn His Ser Phe Lys Gln Asn Val Asp Arg Tyr Ala Leu Leu Ser
                165                 170                 175

Thr Leu Gln Leu Met Tyr Thr Val Gly Tyr Ser Phe Ser Leu Ile Ser
            180                 185                 190

Leu Phe Leu Ala Leu Thr Leu Leu Phe Leu Arg Lys Leu His Cys
        195                 200                 205

Thr Arg Asn Tyr Ile His Met Asn Leu Phe Ala Ser Phe Ile Leu Arg
210                 215                 220

Thr Leu Ala Val Leu Val Lys Asp Val Phe Tyr Asn Ser Tyr Ser
225                 230                 235                 240

Lys Arg Pro Asp Asn Glu Asn Gly Trp Met Ser Tyr Leu Ser Glu Met
                245                 250                 255

Ser Thr Ser Cys Arg Ser Val Gln Val Leu Leu His Tyr Phe Val Gly
            260                 265                 270

Ala Asn Tyr Leu Trp Leu Leu Val Glu Gly Leu Tyr Leu His Thr Leu
        275                 280                 285

Leu Glu Pro Thr Val Leu Pro Glu Arg Arg Leu Trp Pro Arg Tyr Leu
    290                 295                 300

Leu Leu Gly Trp Ala Phe Pro Val Leu Phe Val Val Pro Trp Gly Phe
305                 310                 315                 320

Ala Arg Ala His Leu Glu Asn Thr Gly Cys Trp Thr Thr Asn Gly Asn
                325                 330                 335

Lys Lys Ile Trp Trp Ile Ile Arg Gly Pro Met Met Leu Cys Val Thr
            340                 345                 350

Val Asn Phe Phe Ile Phe Leu Lys Ile Leu Lys Leu Leu Ile Ser Lys
        355                 360                 365

```
Leu Lys Ala His Gln Met Cys Phe Arg Asp Tyr Lys Tyr Arg Leu Ala
    370                 375                 380

Lys Ser Thr Leu Val Leu Ile Pro Leu Leu Gly Val His Glu Ile Leu
385                 390                 395                 400

Phe Ser Phe Ile Thr Asp Asp Gln Val Glu Gly Phe Ala Lys Leu Ile
                    405                 410                 415

Arg Leu Phe Ile Gln Leu Thr Leu Ser Ser Phe His Gly Phe Leu Val
                420                 425                 430

Ala Leu Gln Tyr Gly Phe Ala Asn Gly Glu Val Lys Ala Glu Leu Arg
            435                 440                 445

Lys Tyr Trp Val Arg Phe Leu Leu Ala Arg His Ser Gly Cys Arg Ala
        450                 455                 460

Cys Val Leu Gly Lys Asp Phe Arg Phe Leu Gly Lys Cys Pro Lys Lys
465                 470                 475                 480

Leu Ser Glu Gly Asp Gly Ala Glu Lys Leu Arg Lys Leu Gln Pro Ser
                    485                 490                 495

Leu Asn Ser Gly Arg Leu Leu His Leu Ala Met Arg Gly Leu Gly Glu
                500                 505                 510

Leu Gly Ala Gln Pro Gln Gln Asp His Ala Arg Trp Pro Arg Gly Ser
            515                 520                 525

Ser Leu Ser Glu Cys Ser Glu Gly Asp Val Thr Met Ala Asn Thr Met
        530                 535                 540

Glu Glu Ile Leu Glu Glu Ser Glu Ile
545                 550

<210> SEQ ID NO 36
<211> LENGTH: 553
<212> TYPE: PRT
<213> ORGANISM: Artificial Sequence
<220> FEATURE:
<223> OTHER INFORMATION: GLP 2R Variant

<400> SEQUENCE: 36

Met Lys Leu Gly Ser Ser Arg Ala Gly Pro Gly Arg Gly Ser Ala Gly
  1               5                  10                  15

Leu Leu Pro Gly Val His Glu Leu Pro Met Gly Ile Pro Ala Pro Trp
                20                  25                  30

Gly Thr Ser Pro Leu Ser Phe His Arg Lys Cys Ser Leu Trp Ala Pro
             35                  40                  45

Gly Arg Pro Phe Leu Thr Leu Val Leu Leu Val Ser Ile Lys Gln Val
         50                  55                  60

Thr Gly Ser Leu Leu Glu Glu Thr Thr Arg Lys Trp Ala Gln Tyr Lys
 65                  70                  75                  80

Gln Ala Cys Leu Arg Asp Leu Leu Lys Glu Pro Ser Gly Ile Phe Cys
                 85                  90                  95

Asn Gly Thr Phe Asp Gln Tyr Val Cys Trp Pro His Ser Ser Pro Gly
                100                 105                 110

Asn Val Ser Val Pro Cys Pro Ser Tyr Leu Pro Trp Trp Ser Glu Glu
            115                 120                 125

Ser Ser Gly Arg Ala Tyr Arg His Cys Leu Ala Gln Gly Thr Trp Gln
        130                 135                 140

Thr Ile Glu Asn Ala Thr Asp Ile Trp Gln Asp Asp Ser Glu Cys Ser
145                 150                 155                 160

Glu Asn His Ser Phe Lys Gln Asn Val Asp Arg Tyr Ala Leu Leu Ser
                165                 170                 175
```

```
Thr Leu Gln Leu Met Tyr Thr Val Gly Tyr Ser Phe Ser Leu Ile Ser
            180                 185                 190
Leu Phe Leu Ala Leu Thr Leu Leu Phe Leu Arg Lys Leu His Cys
        195                 200                 205
Thr Arg Asn Tyr Ile His Met Asn Leu Phe Ala Ser Phe Ile Leu Arg
    210                 215                 220
Thr Leu Ala Val Leu Val Lys Asp Val Val Phe Tyr Asn Ser Tyr Ser
225                 230                 235                 240
Lys Arg Pro Asp Asn Glu Asn Gly Trp Met Ser Tyr Leu Ser Glu Met
                245                 250                 255
Ser Thr Ser Cys Arg Ser Val Gln Val Leu Leu His Tyr Phe Val Gly
            260                 265                 270
Ala Asn Tyr Leu Trp Leu Leu Val Glu Gly Leu Tyr Leu His Thr Leu
        275                 280                 285
Leu Glu Pro Thr Val Leu Pro Glu Arg Arg Leu Trp Pro Arg Tyr Leu
    290                 295                 300
Leu Leu Gly Trp Ala Phe Pro Val Leu Phe Val Val Pro Trp Gly Phe
305                 310                 315                 320
Ala Arg Ala His Leu Glu Asn Thr Gly Cys Trp Thr Thr Asn Gly Asn
                325                 330                 335
Lys Lys Ile Trp Trp Ile Ile Arg Gly Pro Met Met Leu Cys Val Thr
            340                 345                 350
Val Asn Phe Phe Ile Phe Leu Lys Ile Leu Lys Leu Leu Ile Ser Lys
        355                 360                 365
Leu Lys Ala His Gln Met Cys Phe Arg Asp Tyr Lys Tyr Arg Leu Ala
    370                 375                 380
Lys Ser Thr Leu Val Leu Ile Pro Leu Leu Gly Val His Glu Ile Leu
385                 390                 395                 400
Phe Ser Phe Ile Thr Asp Asp Gln Val Glu Gly Phe Ala Lys Leu Ile
                405                 410                 415
Arg Leu Phe Ile Gln Leu Thr Leu Ser Ser Phe His Gly Phe Leu Val
            420                 425                 430
Ala Leu Gln Tyr Gly Phe Ala Asn Gly Glu Val Lys Ala Glu Leu Arg
        435                 440                 445
Lys Tyr Trp Val Arg Phe Leu Leu Ala Arg His Ser Gly Cys Arg Ala
    450                 455                 460
Cys Val Leu Gly Lys Asp Phe Arg Phe Leu Gly Lys Cys Pro Lys Lys
465                 470                 475                 480
Leu Ser Glu Gly Asp Gly Ala Glu Lys Leu Arg Lys Leu Gln Pro Ser
                485                 490                 495
Leu Asn Ser Gly Arg Leu Leu His Leu Ala Met Arg Gly Leu Ala Asp
            500                 505                 510
Val Gly Ala Gln Pro Gln Gln Asp His Ala Arg Trp Pro Arg Gly Ser
        515                 520                 525
Ser Leu Ser Glu Cys Ser Glu Gly Asp Val Thr Met Ala Asn Thr Met
    530                 535                 540
Glu Glu Ile Leu Glu Glu Ser Glu Ile
545                 550

<210> SEQ ID NO 37
<211> LENGTH: 59
<212> TYPE: DNA
<213> ORGANISM: Artificial Sequence
<220> FEATURE:
```

<210> SEQ ID NO 37
<211> LENGTH: 59
<212> TYPE: DNA
<213> ORGANISM: Artificial Sequence
<220> FEATURE:
<223> OTHER INFORMATION: Primer

<400> SEQUENCE: 37
ccaaagtata caggcgcata gcgatggttc tttctctgat gagatgaaca ccattcttg    59

<210> SEQ ID NO 38
<211> LENGTH: 65
<212> TYPE: DNA
<213> ORGANISM: Artificial Sequence
<220> FEATURE:
<223> OTHER INFORMATION: Primer

<400> SEQUENCE: 38
ttggtctgaa tcaaccagtt tataaagtct cgagcggcaa gattatcaag aatggtgttc    60
atctc    65

<210> SEQ ID NO 39
<211> LENGTH: 27
<212> TYPE: DNA
<213> ORGANISM: Artificial Sequence
<220> FEATURE:
<223> OTHER INFORMATION: Primer

<400> SEQUENCE: 39
tttgcggccg cccaaagtat acaggcg    27

<210> SEQ ID NO 40
<211> LENGTH: 37
<212> TYPE: DNA
<213> ORGANISM: Artificial Sequence
<220> FEATURE:
<223> OTHER INFORMATION: Primer

<400> SEQUENCE: 40
aaaggatccg tcagtgattt tggtctgaat caaccag    37

<210> SEQ ID NO 41
<211> LENGTH: 59
<212> TYPE: DNA
<213> ORGANISM: Artificial Sequence
<220> FEATURE:
<223> OTHER INFORMATION: Primer

<400> SEQUENCE: 41
ccaaagtata caggcgcatg gcgatggttc tttctctgat gagatgaaca ccattcttg    59

<210> SEQ ID NO 42
<211> LENGTH: 59
<212> TYPE: PRT
<213> ORGANISM: Artificial Sequence
<220> FEATURE:
<223> OTHER INFORMATION: Mimetibody

<400> SEQUENCE: 42

His Gly Asp Gly Ser Phe Ser Asp Glu Met Asn Thr Ile Leu Asp Asn
 1               5                  10                  15
Leu Ala Ala Arg Asp Phe Ile Asn Trp Leu Ile Gln Thr Lys Ile Thr
            20                  25                  30
Asp Gly Ser Gly Gly Ser Gly Ala Leu Val Pro Val Ser Ser Glu
        35                  40                  45
Ser Lys Tyr Gly Pro Pro Cys Pro Pro Cys Pro
    50                  55

<210> SEQ ID NO 43
<211> LENGTH: 59
<212> TYPE: PRT
<213> ORGANISM: Artificial Sequence
<220> FEATURE:
<223> OTHER INFORMATION: Mimetibody

<400> SEQUENCE: 43

```
His Gly Asp Gly Ser Phe Ser Asp Glu Met Asn Thr Ile Leu Asp Asn
  1               5                  10                  15

Leu Ala Ala Arg Asp Phe Ile Asn Trp Leu Ile Gln Thr Lys Ile Thr
             20                  25                  30

Asp Gly Ser Gly Gly Gly Ser Gly Ala Leu Val Ala Val Pro Ser Glu
         35                  40                  45

Ser Lys Tyr Gly Pro Pro Cys Pro Pro Cys Pro
     50                  55
```

<210> SEQ ID NO 44
<211> LENGTH: 59
<212> TYPE: PRT
<213> ORGANISM: Artificial Sequence
<220> FEATURE:
<223> OTHER INFORMATION: Mimetibody

<400> SEQUENCE: 44

```
His Gly Asp Gly Ser Phe Ser Asp Glu Met Asn Thr Ile Leu Asp Asn
  1               5                  10                  15

Leu Ala Ala Arg Asp Phe Ile Asn Trp Leu Ile Gln Thr Lys Ile Thr
             20                  25                  30

Asp Gly Ser Gly Gly Gly Ser Gly Ala Leu Val Ala Val Ser Pro Glu
         35                  40                  45

Ser Lys Tyr Gly Pro Pro Cys Pro Pro Cys Pro
     50                  55
```

<210> SEQ ID NO 45
<211> LENGTH: 59
<212> TYPE: PRT
<213> ORGANISM: Artificial Sequence
<220> FEATURE:
<223> OTHER INFORMATION: Mimetibody

<400> SEQUENCE: 45

```
His Gly Asp Gly Ser Phe Ser Asp Glu Met Asn Thr Ile Leu Asp Asn
  1               5                  10                  15

Leu Ala Ala Arg Asp Phe Ile Asn Trp Leu Ile Gln Thr Lys Ile Thr
             20                  25                  30

Asp Gly Ser Gly Gly Gly Ser Gly Ala Leu Val Ala Val Ser Ser Glu
         35                  40                  45

Ser Lys Pro Gly Pro Pro Cys Pro Pro Cys Pro
     50                  55
```

<210> SEQ ID NO 46
<211> LENGTH: 177
<212> TYPE: DNA
<213> ORGANISM: Artificial Sequence
<220> FEATURE:
<223> OTHER INFORMATION: Mimetibody

<400> SEQUENCE: 46

```
catggcgatg gttctttctc tgatgagatg aacaccattc ttgataatct tgccgctcga      60
gactttataa actggttgat tcagaccaaa atcactgacg gatccggtgg aggctccggt     120
```

```
gccttagtcc ccgtctcctc agagtccaaa tatggtcccc catgcccacc atgcccg      177
```

```
<210> SEQ ID NO 47
<211> LENGTH: 176
<212> TYPE: DNA
<213> ORGANISM: Artificial Sequence
<220> FEATURE:
<223> OTHER INFORMATION: Mimetibody

<400> SEQUENCE: 47
atggcgatgg ttctttctct gatgagatga acaccattct tgataatctt gccgctcgag      60
actttataaa ctggttgatt cagaccaaaa tcactgacgg atccggtgga ggctccggtg     120
ccttagtcgc cgtcccctca gagtccaaat atggtccccc atgcccacca tgcccg         176

<210> SEQ ID NO 48
<211> LENGTH: 177
<212> TYPE: DNA
<213> ORGANISM: Artificial Sequence
<220> FEATURE:
<223> OTHER INFORMATION: Mimetibody

<400> SEQUENCE: 48
catggcgatg gttctttctc tgatgagatg aacaccattc ttgataatct tgccgctcga      60
gactttataa actggttgat tcagaccaaa atcactgacg gatccggtgg aggctccggt     120
gccttagtcg ccgtctcccc agagtccaaa tatggtcccc catgcccacc atgcccg        177

<210> SEQ ID NO 49
<211> LENGTH: 177
<212> TYPE: DNA
<213> ORGANISM: Artificial Sequence
<220> FEATURE:
<223> OTHER INFORMATION: Mimetibody

<400> SEQUENCE: 49
catggcgatg gttctttctc tgatgagatg aacaccattc ttgataatct tgccgctcga      60
gactttataa actggttgat tcagaccaaa atcactgacg gatccggtgg aggctccggt     120
gccttagtcg ccgtctcctc agagtccaaa cctggtcccc catgcccacc atgcccg        177

<210> SEQ ID NO 50
<211> LENGTH: 33
<212> TYPE: PRT
<213> ORGANISM: Artificial Sequence
<220> FEATURE:
<223> OTHER INFORMATION: GLP-2 variant

<400> SEQUENCE: 50

His Gly Asp Gly Ser Phe Ser Ser Asp Met Ser Thr Ile Leu Asp Asn
  1               5                  10                  15

Leu Ala Ala Arg Asp Phe Ile Asn Trp Leu Ile Gln Thr Lys Ile Thr
             20                  25                  30

Asp

<210> SEQ ID NO 51
<211> LENGTH: 33
<212> TYPE: PRT
<213> ORGANISM: Artificial Sequence
<220> FEATURE:
<223> OTHER INFORMATION: GLP-2 variant

<400> SEQUENCE: 51

His Gly Asp Gly Ser Phe Ser Ser Asp Val Ser Thr Ile Leu Asp Asn
```

```
                   1               5                  10                  15
Leu Ala Ala Arg Asp Phe Ile Asn Trp Leu Ile Gln Thr Lys Ile Thr
            20                  25                  30

Asp

<210> SEQ ID NO 52
<211> LENGTH: 33
<212> TYPE: PRT
<213> ORGANISM: Artificial Sequence
<220> FEATURE:
<223> OTHER INFORMATION: GLP-2 variant

<400> SEQUENCE: 52

His Gly Asp Gly Ser Phe Ser Asp Glu Met Asn Thr Tyr Leu Asp Asn
  1               5                  10                  15

Leu Ala Ala Arg Asp Phe Ile Asn Trp Leu Ile Gln Thr Lys Ile Thr
            20                  25                  30

Asp

<210> SEQ ID NO 53
<211> LENGTH: 33
<212> TYPE: PRT
<213> ORGANISM: Artificial Sequence
<220> FEATURE:
<223> OTHER INFORMATION: GLP-2 variant

<400> SEQUENCE: 53

His Gly Asp Gly Ser Phe Ser Asp Glu Met Asn Thr Ile Leu Asp Gly
  1               5                  10                  15

Leu Ala Ala Arg Asp Phe Ile Asn Trp Leu Ile Gln Thr Lys Ile Thr
            20                  25                  30

Asp

<210> SEQ ID NO 54
<211> LENGTH: 33
<212> TYPE: PRT
<213> ORGANISM: Artificial Sequence
<220> FEATURE:
<223> OTHER INFORMATION: GLP-2 variant

<400> SEQUENCE: 54

His Gly Asp Gly Ser Phe Ser Asp Glu Met Asn Thr Ile Leu Asp Asn
  1               5                  10                  15

Gln Ala Ala Arg Asp Phe Ile Asn Trp Leu Ile Gln Thr Lys Ile Thr
            20                  25                  30

Asp

<210> SEQ ID NO 55
<211> LENGTH: 33
<212> TYPE: PRT
<213> ORGANISM: Artificial Sequence
<220> FEATURE:
<223> OTHER INFORMATION: GLP-2 variant

<400> SEQUENCE: 55

His Gly Asp Gly Ser Phe Ser Asp Glu Met Asn Thr Ile Leu Asp Gly
  1               5                  10                  15

Gln Ala Ala Arg Asp Phe Ile Asn Trp Leu Ile Gln Thr Lys Ile Thr
            20                  25                  30

Asp
```

<210> SEQ ID NO 56
<211> LENGTH: 33
<212> TYPE: PRT
<213> ORGANISM: Artificial Sequence
<220> FEATURE:
<223> OTHER INFORMATION: GLP-2 variant

<400> SEQUENCE: 56

His Gly Asp Gly Ser Phe Ser Asp Glu Met Asn Thr Ile Leu Asp Asn
1               5                   10                  15

Leu Ala Ala Arg Asp Phe Ile Ala Trp Leu Ile Gln Thr Lys Ile Thr
            20                  25                  30

Asp

<210> SEQ ID NO 57
<211> LENGTH: 33
<212> TYPE: PRT
<213> ORGANISM: Artificial Sequence
<220> FEATURE:
<223> OTHER INFORMATION: GLP-2 variant

<400> SEQUENCE: 57

His Gly Asp Gly Ser Phe Ser Asp Glu Met Asn Thr Ile Leu Asp Asn
1               5                   10                  15

Leu Ala Ala Arg Asp Phe Ile Asn Trp Leu Val Lys Gly Lys Ile Thr
            20                  25                  30

Asp

<210> SEQ ID NO 58
<211> LENGTH: 59
<212> TYPE: PRT
<213> ORGANISM: Artificial Sequence
<220> FEATURE:
<223> OTHER INFORMATION: Mimetibody

<400> SEQUENCE: 58

His Gly Asp Gly Ser Phe Ser Ser Asp Met Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Ser Gly Gly Gly Ser Gly Thr Leu Val Thr Val Ser Ser Glu
            35                  40                  45

Ser Lys Tyr Gly Pro Pro Cys Pro Pro Cys Pro
    50                  55

<210> SEQ ID NO 59
<211> LENGTH: 59
<212> TYPE: PRT
<213> ORGANISM: Artificial Sequence
<220> FEATURE:
<223> OTHER INFORMATION: Mimetibody

<400> SEQUENCE: 59

His Gly Asp Gly Ser Phe Ser Ser Asp Val Ser Thr Ile Leu Asp Asn
1               5                   10                  15

Leu Ala Ala Arg Asp Phe Ile Asn Trp Leu Ile Gln Thr Lys Ile Thr
            20                  25                  30

Asp Gly Ser Gly Gly Gly Ser Gly Thr Leu Val Thr Val Ser Ser Glu
            35                  40                  45

Ser Lys Tyr Gly Pro Pro Cys Pro Pro Cys Pro
    50                  55

<210> SEQ ID NO 60
<211> LENGTH: 59
<212> TYPE: PRT
<213> ORGANISM: Artificial Sequence
<220> FEATURE:
<223> OTHER INFORMATION: Mimetibody

<400> SEQUENCE: 60

His Gly Asp Gly Ser Phe Ser Asp Glu Met Asn Thr Tyr Leu Asp Asn
1               5                   10                  15

Leu Ala Ala Arg Asp Phe Ile Asn Trp Leu Ile Gln Thr Lys Ile Thr
            20                  25                  30

Asp Gly Ser Gly Gly Gly Ser Gly Thr Leu Val Thr Val Ser Ser Glu
        35                  40                  45

Ser Lys Tyr Gly Pro Pro Cys Pro Pro Cys Pro
    50                  55

<210> SEQ ID NO 61
<211> LENGTH: 59
<212> TYPE: PRT
<213> ORGANISM: Artificial Sequence
<220> FEATURE:
<223> OTHER INFORMATION: Mimetibody

<400> SEQUENCE: 61

His Gly Asp Gly Ser Phe Ser Asp Glu Met Asn Thr Ile Leu Asp Gly
1               5                   10                  15

Leu Ala Ala Arg Asp Phe Ile Asn Trp Leu Ile Gln Thr Lys Ile Thr
            20                  25                  30

Asp Gly Ser Gly Gly Gly Ser Gly Thr Leu Val Thr Val Ser Ser Glu
        35                  40                  45

Ser Lys Tyr Gly Pro Pro Cys Pro Pro Cys Pro
    50                  55

<210> SEQ ID NO 62
<211> LENGTH: 59
<212> TYPE: PRT
<213> ORGANISM: Artificial Sequence
<220> FEATURE:
<223> OTHER INFORMATION: Mimetibody

<400> SEQUENCE: 62

His Gly Asp Gly Ser Phe Ser Asp Glu Met Asn Thr Ile Leu Asp Asn
1               5                   10                  15

Gln Ala Ala Arg Asp Phe Ile Asn Trp Leu Ile Gln Thr Lys Ile Thr
            20                  25                  30

Asp Gly Ser Gly Gly Gly Ser Gly Thr Leu Val Thr Val Ser Ser Glu
        35                  40                  45

Ser Lys Tyr Gly Pro Pro Cys Pro Pro Cys Pro
    50                  55

<210> SEQ ID NO 63
<211> LENGTH: 59
<212> TYPE: PRT
<213> ORGANISM: Artificial Sequence
<220> FEATURE:
<223> OTHER INFORMATION: Mimetibody

<400> SEQUENCE: 63

His Gly Asp Gly Ser Phe Ser Asp Glu Met Asn Thr Ile Leu Asp Gly
1               5                   10                  15

Gln Ala Ala Arg Asp Phe Ile Asn Trp Leu Ile Gln Thr Lys Ile Thr
            20                  25                  30

Asp Gly Ser Gly Gly Gly Ser Gly Thr Leu Val Thr Val Ser Ser Glu
        35                  40                  45

Ser Lys Tyr Gly Pro Pro Cys Pro Pro Cys Pro
    50                  55

<210> SEQ ID NO 64
<211> LENGTH: 59
<212> TYPE: PRT
<213> ORGANISM: Artificial Sequence
<220> FEATURE:
<223> OTHER INFORMATION: Mimetibody

<400> SEQUENCE: 64

His Gly Asp Gly Ser Phe Ser Asp Glu Met Asn Thr Ile Leu Asp Asn
1               5                   10                  15

Leu Ala Ala Arg Asp Phe Ile Ala Trp Leu Ile Gln Thr Lys Ile Thr
            20                  25                  30

Asp Gly Ser Gly Gly Gly Ser Gly Thr Leu Val Thr Val Ser Ser Glu
        35                  40                  45

Ser Lys Tyr Gly Pro Pro Cys Pro Pro Cys Pro
    50                  55

<210> SEQ ID NO 65
<211> LENGTH: 59
<212> TYPE: PRT
<213> ORGANISM: Artificial Sequence
<220> FEATURE:
<223> OTHER INFORMATION: Mimetibody

<400> SEQUENCE: 65

His Gly Asp Gly Ser Phe Ser Asp Glu Met Asn Thr Ile Leu Asp Asn
1               5                   10                  15

Leu Ala Ala Arg Asp Phe Ile Asn Trp Leu Val Lys Gly Lys Ile Thr
            20                  25                  30

Asp Gly Ser Gly Gly Gly Ser Gly Thr Leu Val Thr Val Ser Ser Glu
        35                  40                  45

Ser Lys Tyr Gly Pro Pro Cys Pro Pro Cys Pro
    50                  55

<210> SEQ ID NO 66
<211> LENGTH: 177
<212> TYPE: DNA
<213> ORGANISM: Artificial Sequence
<220> FEATURE:
<223> OTHER INFORMATION: Mimetibody

<400> SEQUENCE: 66
catggcgatg gttctttctc tagtgacatg tcgaccattc ttgataatct tgccgctcga      60
gactttataa actggttgat tcagaccaaa atcactgacg gatccggtgg aggctccggt     120
accttagtca ccgtctcctc agagtccaaa tatggtcccc catgcccacc atgcccg        177

<210> SEQ ID NO 67
<211> LENGTH: 177
<212> TYPE: DNA
<213> ORGANISM: Artificial Sequence
<220> FEATURE:
<223> OTHER INFORMATION: Mimetibody

<400> SEQUENCE: 67

```
catggcgatg gttctttctc tagtgacgtc tcgaccattc ttgataatct tgccgctcga    60
gactttataa actggttgat tcagaccaaa atcactgacg gatccggtgg aggctccggt   120
accttagtca ccgtctcctc agagtccaaa tatggtcccc catgcccacc atgcccg      177

<210> SEQ ID NO 68
<211> LENGTH: 177
<212> TYPE: DNA
<213> ORGANISM: Artificial Sequence
<220> FEATURE:
<223> OTHER INFORMATION: Mimetibody

<400> SEQUENCE: 68
catggcgatg gttctttctc tgatgagatg aacacctatc ttgataatct tgccgctcga    60
gactttataa actggttgat tcagaccaaa atcactgacg gatccggtgg aggctccggt   120
accttagtca ccgtctcctc agagtccaaa tatggtcccc catgcccacc atgcccg      177

<210> SEQ ID NO 69
<211> LENGTH: 177
<212> TYPE: DNA
<213> ORGANISM: Artificial Sequence
<220> FEATURE:
<223> OTHER INFORMATION: Mimetibody

<400> SEQUENCE: 69
catggcgatg gttctttctc tgatgagatg aacaccattc ttgatggtct tgccgctcga    60
gactttataa actggttgat tcagaccaaa atcactgacg gatccggtgg aggctccggt   120
accttagtca ccgtctcctc agagtccaaa tatggtcccc catgcccacc atgcccg      177

<210> SEQ ID NO 70
<211> LENGTH: 177
<212> TYPE: DNA
<213> ORGANISM: Artificial Sequence
<220> FEATURE:
<223> OTHER INFORMATION: Mimetibody

<400> SEQUENCE: 70
catggcgatg gttctttctc tgatgagatg aacaccattc ttgataatca ggccgctcga    60
gactttataa actggttgat tcagaccaaa atcactgacg gatccggtgg aggctccggt   120
accttagtca ccgtctcctc agagtccaaa tatggtcccc catgcccacc atgcccg      177

<210> SEQ ID NO 71
<211> LENGTH: 177
<212> TYPE: DNA
<213> ORGANISM: Artificial Sequence
<220> FEATURE:
<223> OTHER INFORMATION: Mimetibody

<400> SEQUENCE: 71
catggcgatg gttctttctc tgatgagatg aacaccattc ttgatggcca ggccgctcga    60
gactttataa actggttgat tcagaccaaa atcactgacg gatccggtgg aggctccggt   120
accttagtca ccgtctcctc agagtccaaa tatggtcccc catgcccacc atgcccg      177

<210> SEQ ID NO 72
<211> LENGTH: 177
<212> TYPE: DNA
<213> ORGANISM: Artificial Sequence
<220> FEATURE:
<223> OTHER INFORMATION: Mimetibody
```

-continued

```
<400> SEQUENCE: 72
catggcgatg gttctttctc tgatgagatg aacaccattc ttgataatct tgccgctcga    60
gactttatag cctggttgat tcagaccaaa atcactgacg gatccggtgg aggctccggt   120
accttagtca ccgtctcctc agagtccaaa tatggtcccc catgcccacc atgcccg      177

<210> SEQ ID NO 73
<211> LENGTH: 177
<212> TYPE: DNA
<213> ORGANISM: Artificial Sequence
<220> FEATURE:
<223> OTHER INFORMATION: Mimetibody

<400> SEQUENCE: 73
catggcgatg gttctttctc tgatgagatg aacaccattc ttgataatct tgccgctcga    60
gactttataa actggttggt taagggcaaa atcactgacg gatccggtgg aggctccggt   120
accttagtca ccgtctcctc agagtccaaa tatggtcccc catgcccacc atgcccg      177

<210> SEQ ID NO 74
<211> LENGTH: 33
<212> TYPE: PRT
<213> ORGANISM: Artificial Sequence
<220> FEATURE:
<223> OTHER INFORMATION: GLP-2 Peptide with A2G, M10V mutation

<400> SEQUENCE: 74

His Gly Asp Gly Ser Phe Ser Asp Glu Val Asn Thr Ile Leu Asp Asn
 1               5                  10                  15

Leu Ala Ala Arg Asp Phe Ile Asn Trp Leu Ile Gln Thr Lys Ile
            20                  25                  30

Thr Asp

<210> SEQ ID NO 75
<211> LENGTH: 276
<212> TYPE: PRT
<213> ORGANISM: Artificial Sequence
<220> FEATURE:
<223> OTHER INFORMATION: GLP-2 Mimetibody amino acid sequence with A2G,
      L17Q mutation

<400> SEQUENCE: 75

His Gly Asp Gly Ser Phe Ser Asp Glu Met Asn Thr Ile Leu Asp Asn
 1               5                  10                  15

Gln Ala Ala Arg Asp Phe Ile Asn Trp Leu Ile Gln Thr Lys Ile Thr
            20                  25                  30

Asp Gly Ser Gly Gly Gly Ser Gly Thr Leu Val Thr Val Ser Ser Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140
```

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly Lys
        275

<210> SEQ ID NO 76
<211> LENGTH: 828
<212> TYPE: DNA
<213> ORGANISM: Artificial Sequence
<220> FEATURE:
<223> OTHER INFORMATION: GLP-2 Mimetibody nucleic acid sequence with
      A2G, L17Q mutation

<400> SEQUENCE: 76
catggcgatg gttctttctc tgatgagatg aacaccattc ttgataatca ggccgctcga      60
gactttataa actggttgat tcagaccaaa atcactgacg atccggtgg aggctccggt     120 accttagtca ccgtctcctc agagtccaaa tatggtcccc catgcccacc atgcccggcg     180
cctgaggccg ccggggacc atcagtcttc ctgttccccc caaaacccaa ggacactctc     240
atgatctccc ggacccctga ggtcacgtgc gtggtggtgg acgtgagcca ggaagacccc     300
gaggtccagt tcaactggta cgtggatggc gtggaggtgc ataatgccaa gacaaagccg     360
cgggaggagc agttcaacag cacgtaccgt gtggtcagcg tcctcaccgt cctgcaccag     420
gactggctga acggcaagga gtacaagtgc aaggtctcca acaaaggcct cccgtcctcc     480
atcgagaaaa ccatctccaa agccaaaggg cagcctcgag agccacaggt gtacaccctg     540
cccccatccc aggaggagat gaccaagaac caggtcagcc tgacctgcct ggtcaaaggc     600
ttctacccca gcgacatcgc cgtggagtgg gagagcaatg ggcagccgga gaacaactac     660
aagaccacgc ctcccgtgct ggactccgac ggctccttct tcctctacag caggctaacc     720
gtggacaaga gcaggtggca ggaggggaat gtcttctcat gctccgtgat gcatgaggct     780
ctgcacaacc actacacaca gaaaagcttg tccctgtctc tgggtaaa                 828

<210> SEQ ID NO 77
<211> LENGTH: 276
<212> TYPE: PRT
<213> ORGANISM: Artificial Sequence
<220> FEATURE:
<223> OTHER INFORMATION: GLP-2 Mimetibody nucleic acid sequence with
      A2G, N16G, L17Q mutation

<400> SEQUENCE: 77

His Gly Asp Gly Ser Phe Ser Asp Glu Met Asn Thr Ile Leu Asp Gly

```
                1               5                   10                  15
           Gln Ala Ala Arg Asp Phe Ile Asn Trp Leu Ile Gln Thr Lys Ile Thr
                            20                  25                  30

Asp Gly Ser Gly Gly Ser Gly Thr Leu Val Thr Val Ser Ser Glu
                        35                  40                  45

Ser Lys Tyr Gly Pro Pro Cys Pro Cys Pro Ala Pro Glu Ala Ala
                    50                  55                  60

Gly Gly Pro Ser Val Phe Leu Phe Pro Pro Lys Pro Lys Asp Thr Leu
            65                  70                  75                  80

Met Ile Ser Arg Thr Pro Glu Val Thr Cys Val Val Val Asp Val Ser
                            85                  90                  95

Gln Glu Asp Pro Glu Val Gln Phe Asn Trp Tyr Val Asp Gly Val Glu
                        100                 105                 110

Val His Asn Ala Lys Thr Lys Pro Arg Glu Glu Gln Phe Asn Ser Thr
                    115                 120                 125

Tyr Arg Val Val Ser Val Leu Thr Val Leu His Gln Asp Trp Leu Asn
                130                 135                 140

Gly Lys Glu Tyr Lys Cys Lys Val Ser Asn Lys Gly Leu Pro Ser Ser
           145                 150                 155                 160

Ile Glu Lys Thr Ile Ser Lys Ala Lys Gly Gln Pro Arg Glu Pro Gln
                            165                 170                 175

Val Tyr Thr Leu Pro Pro Ser Gln Glu Glu Met Thr Lys Asn Gln Val
                        180                 185                 190

Ser Leu Thr Cys Leu Val Lys Gly Phe Tyr Pro Ser Asp Ile Ala Val
                    195                 200                 205

Glu Trp Glu Ser Asn Gly Gln Pro Glu Asn Asn Tyr Lys Thr Thr Pro
                210                 215                 220

Pro Val Leu Asp Ser Asp Gly Ser Phe Phe Leu Tyr Ser Arg Leu Thr
           225                 230                 235                 240

Val Asp Lys Ser Arg Trp Gln Glu Gly Asn Val Phe Ser Cys Ser Val
                            245                 250                 255

Met His Glu Ala Leu His Asn His Tyr Thr Gln Lys Ser Leu Ser Leu
                        260                 265                 270

Ser Leu Gly Lys
                    275

<210> SEQ ID NO 78
<211> LENGTH: 828
<212> TYPE: DNA
<213> ORGANISM: Artificial Sequence
<220> FEATURE:
<223> OTHER INFORMATION: GLP-2 Mimetibody nucleic acid sequence with
      A2G, N16G, L17Q mutation

<400> SEQUENCE: 78
catggcgatg gttctttctc tgatgagatg aacaccattc ttgatggcca ggccgctcga        60
gactttataa actggttgat tcagaccaaa atcactgacg gatccggtgg aggctccggt       120 acctta gtca ccgtctcctc agagtccaaa tatggtcccc catgcccacc atgcccggcg      180
cctgaggccg ccggggggacc atcagtcttc ctgttccccc caaaacccaa ggacactctc      240
atgatctccc ggacccctga ggtcacgtgc gtggtggtgg acgtgagcca ggaagacccc      300
gaggtccagt tcaactggta cgtggatggc gtggaggtgc ataatgccaa gacaaagccg      360
cgggaggagc agttcaacag cacgtaccgt gtggtcagcg tcctcaccgt cctgcaccag      420
gactggctga acggcaagga gtacaagtgc aaggtctcca acaaaggcct cccgtcctcc      480
```

```
atcgagaaaa ccatctccaa agccaaaggg cagcctcgag agccacaggt gtacaccctg    540
cccccatccc aggaggagat gaccaagaac caggtcagcc tgacctgcct ggtcaaaggc    600
ttctacccca gcgacatcgc cgtggagtgg gagagcaatg ggcagccgga gaacaactac    660
aagaccacgc ctcccgtgct ggactccgac ggctccttct tcctctacag caggctaacc    720
gtggacaaga gcaggtggca ggaggggaat gtcttctcat gctccgtgat gcatgaggct    780
ctgcacaacc actacacaca gaaaagcttg tccctgtctc tgggtaaa                 828
```

<210> SEQ ID NO 79
<211> LENGTH: 30
<212> TYPE: PRT
<213> ORGANISM: Artificial Sequence
<220> FEATURE:
<223> OTHER INFORMATION: GLP-1 Mimetibody amino acid sequence

<400> SEQUENCE: 79

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 80
<211> LENGTH: 280
<212> TYPE: PRT
<213> ORGANISM: Artificial Sequence
<220> FEATURE:
<223> OTHER INFORMATION: Human A2G-GLP2 peptide in murine IgG2a scaffold

<400> SEQUENCE: 80

His Gly Asp Gly Ser Phe Ser Asp Glu Met Asn Thr Ile Leu Asp Asn
 1               5                  10                  15

Leu Ala Ala Arg Asp Phe Ile Asn Trp Leu Ile Gln Thr Lys Ile Thr
            20                  25                  30

Asp Gly Ser Gly Gly Gly Ser Gly Thr Thr Val Thr Val Ser Ala Glu
        35                  40                  45

Pro Arg Gly Pro Thr Ile Lys Pro Cys Pro Pro Cys Lys Cys Pro Ala
    50                  55                  60

Pro Asn Ala Ala Gly Gly Pro Ser Val Phe Ile Phe Pro Pro Lys Ile
65                  70                  75                  80

Lys Asp Val Leu Met Ile Ser Leu Ser Pro Ile Val Thr Cys Val Val
                85                  90                  95

Val Asp Val Ser Glu Asp Asp Pro Asp Val Gln Ile Ser Trp Phe Val
            100                 105                 110

Asn Asn Val Glu Val His Thr Ala Gln Thr Gln Thr His Arg Glu Asp
        115                 120                 125

Tyr Asn Ser Thr Leu Arg Val Val Ser Ala Leu Pro Ile Gln His Gln
    130                 135                 140

Asp Trp Met Ser Gly Lys Glu Phe Lys Cys Lys Val Asn Asn Lys Asp
145                 150                 155                 160

Leu Pro Ala Pro Ile Glu Arg Thr Ile Ser Lys Pro Lys Gly Ser Val
                165                 170                 175

Arg Ala Pro Gln Val Tyr Val Leu Pro Pro Pro Glu Glu Glu Met Thr
            180                 185                 190

Lys Lys Gln Val Thr Leu Thr Cys Met Val Thr Asp Phe Met Pro Glu
        195                 200                 205

Asp Ile Tyr Val Glu Trp Thr Asn Asn Gly Lys Thr Glu Leu Asn Tyr

-continued

```
         210              215              220
Lys Asn Thr Glu Pro Val Leu Asp Ser Asp Gly Ser Tyr Phe Met Tyr
225                 230                 235                 240

Ser Lys Leu Arg Val Glu Lys Lys Asn Trp Val Glu Arg Asn Ser Tyr
                245                 250                 255

Ser Cys Ser Val Val His Glu Gly Leu His Asn His His Thr Thr Lys
                260                 265                 270

Ser Phe Ser Arg Thr Pro Gly Lys
            275                 280
```

GLP-2 MIMETIBODIES, POLYPEPTIDES, COMPOSITIONS, METHODS AND USES

CROSS-REFERENCE TO RELATED APPLICATIONS

This application claims the benefit of U.S. Provisional Application Ser. Nos. 60/824,160, filed 31 Aug. 2006, and 60/862,487, filed 23 Oct. 2006.

FIELD OF THE INVENTION

The present invention relates to mammalian GLP-2 polypeptides and mimetibodies, and their use as therapeutics.

BACKGROUND OF THE INVENTION

Glucagon-like peptide-2 (GLP-2) is a 33 amino acid intestinotrophic peptide hormone generated via post-translational processing of proglucagon (Orskov et al., FEBS Lett. 247: 193-196 (1989); Hartmann et al., Peptides 21: 73-80 (2000)). In mammals, GLP-2 is liberated from proglucagon in the intestine and brain but not in pancreas, as a result of cell-specific expression of prohormone convertases in gut endocrine cells (Dhanvantari et al., Mol. Endocrinol. 10: 342-355 (1996); Rothenberg et al., Mol. Endocrinol. 10: 334-341 (1996); Damholt et al., Endocrinology 140: 4800-4808 (1999); Hoist, Trends Endocrinol Metab. 10: 229-235 (1999)). Analysis of rat and human plasma using a combination of high-performance liquid chromatography and site-specific GLP-2 antisera reveals the presence of two principal circulating molecular forms, GLP-$2^{1-33}$ and GLP-$23^{3-33}$ (Hartmann et al., Supra; Brubaker et al., Endocrinol. 138: 4837-4843 (1997); Hartmann et al., J. Clin. Endocrinol. Metab. 85: 2884-2888 (2000)). GLP-$2^{1-33}$ is cleaved in vivo by the protease dipeptidyl peptidase IV (DPP IV), which removes the first two residues, histidine and alanine (HA). The resulting peptide GLP-$2^{3-33}$ is essentially inactive.

GLP-2 regulates gastric motility, gastric acid secretion, intestinal hexose transport, and increases the barrier function of the gut epithelium (reviewed in Drucker, J. Clin. Endocr. Metab. 86: 1759-1764 (2001)). It significantly enhances the surface area of the mucosal epithelium via stimulation of crypt cell proliferation and inhibition of apoptosis in the enterocyte and crypt compartments. (Drucker et al., Proc. Natl. Acad. Sci. U.S.A. 93: 1911-7916 (1996)). GLP-2 reduces mortality and decreases mucosal injury, cytokine expression, and bacterial septicemia in small and large bowel inflammation (Boushey et al., Am. J. Physiol. 277: E937-E947 (1999); Prasad et al., J. Pediatr. Surg. 35: 357-359 (2000)). GLP-2 also enhances nutrient absorption and gut adaptation in rodents or humans with short bowel syndrome (SBS) (Jeppesen et al., Gastroenterology 120: 806-815 (2001)).

The actions of GLP-2 are transduced by the GLP-2 receptor (GLP-2R), a G protein-coupled receptor expressed in gut endocrine cells of the stomach, small bowel, colon, as well as enteric neurons and subendothelial myofibroblasts (Munroe et al., Proc. Natl. Acad. Sci U.S.A. 96: 1569-1573 (1999); Yusta et al., Gastroenterology 119: 744-755 (2000); Bjerknes et al., Proc. Natl. Acad. Sci. U.S.A. 98: 12497-12502 (2001); Orskov et al., Regul. Pept. 124: 105-112 (2005)). Direct activation of GLP-2R signaling in transfected baby hamster kidney fibroblasts expressing the GLP-2 receptor (BHK-GLP-2R cells) confers resistance to cycloheximide-induced apoptosis (Yusta et al., J. Biol. Chem. 275: 35345-35352 (2000)).

The cytoprotective, reparative, and energy-retentive properties of GLP-2 suggest that GLP-2 may potentially be useful for the treatment of human disorders characterized by injury and/or dysfunction of the intestinal mucosal epithelium. Intestinal epithelial injury is seen in patients with inflammatory bowel disease (IBD), including Crohn's Disease and ulcerative colitis, and in patients with autoimmune diseases that are associated with an inflammatory response in the intestine, such as Celiac's Disease (reviewed in Hanauer, New England J. Med. 334: 841-848 (1996)). In addition, some chemotherapy drugs cause injury to the intestinal epithelium that result in toxic side effects that are dose limiting (Oster, Oncology 13: 41 (1999)). Increased intestinal permeability is also reported in cases of acute pancreatitis (Kouris et al., Am. J. Surg. 181: 571-575 (2001)) and could contribute to food allergies by allowing macromolecules to access the sub-endothelial compartment (Troncone et al., Allergy 49: 142-146 (1994)).

As an important regulatory hormone in nutrient absorption, GLP-2 is also promising in treating patients with short bowel syndrome (SBS) (Drucker et al., Supra; Rubin, Gastroenterol. 117:261-263 (1999); Nightingale, Gut 45: 478-479 (1999)). SBS is defined as malabsorption resulting from anatomical or functional loss of a significant length of the small intestine (reviewed in Jeppesen, J. Nutr. 133: 3721-3724 (2003)). The causes of short bowel syndrome differ between adults and children: in adults, it most often results after surgery for Crohn's disease or mesenteric infarction; while in infants, the causes more commonly include necrotizing enterocolitis, gastroschisis, atresia, and volvulus (Platell et al., World J. Gastroenterol. 8: 13-20 (2002)).

Teduglutide, a DPP-IV resistant GLP-2 peptide analog (where alanine-2 is substituted with glycine (A2G)), is being developed for the potential treatment of gastrointestinal (GI) diseases, including SBS, Crohn's disease and pediatric GI disorders. Teduglutide also has potential for the treatment of mucositis associated with cancer chemotherapy and IBD. However, due to the peptide's low molecular weight, teduglutide is cleared quickly with a half-life of less than 30 minutes. Accordingly, daily dosing is required to maintain the therapeutic level (Shin et al., Curr. Opin. Endocrin. Diabetes 12: 63-71 (2005)). Therefore, a need exists for a modified GLP-2 that will overcome the short half-life while retaining its function and provide for facile development and manufacture.

Inflammatory ileus, the temporary impairment of coordinated gastrointestinal motility following invasive surgery or traumatic injury, remains a major clinical problem, extending hospital stays and often contributing to medical complications during the recovery period (Holte and Kehlet, Br. J. Surg. 87: 1480-1493 (2000)). Ileus is characterized by delayed gastric emptying, dilatation of the small bowel and colon, abdominal distension, loss of normal propulsive contractile patterns, and inability to evacuate gas or stool, leading to prolonged patient discomfort (abdominal distension, nausea, emesis).

In susceptible individuals, such as the elderly or patients with cardiopulmonary compromise, ileus can lead to more serious complications including acute gastric dilatation, cardiac arrhythmia, respiratory distress, aspiration pneumonia, and failure of surgical anastomoses. In severe cases, prolonged loss of the normal "housekeeping" contractile activity of the GI tract can contribute to bacterial overgrowth and breakdown of intestinal barrier function, followed by bacterial translocation and entry into the systemic circulation (Anup and Balasubramanian, J. Surg. Res. 92: 291-300 (2000)). This in turn can lead to endotoxemia, sepsis, multiorgan failure and ultimately death, an outcome for which elderly patients are the most susceptible. Even in the absence of complications, the return of normal bowel function is a prime limiting factor for release of patients from hospital, with inflammatory ileus increasing hospital stays by 3 to 5 days. Thus, costs accrued from increased morbidity and protracted hospital stays can be substantial.

Factors that contribute to the development and maintenance of ileus include the activation of central sympathetic inhibitory reflexes which release norepinephrine into the bowel wall, inhibitory humoral agents, anesthetic and analgesic agents, and inflammatory mediators (Livingston and Passaro, Dig. Dis. Sci. 35: 121-132 (1990); Bauer et al., Curr. Opin. Crit. Care 8: 152-157 (2002)). Results from rodent studies suggest that inflammation within the wall of the GI tract plays a central role in initiating and maintaining ileus.

Studies employing rodent models of post-operative ileus demonstrate that the muscularis externa is a highly immunologically active compartment. Normally resident within the muscularis externa is an impressive array of common leukocytes (Mikkelsen, Histol. Histopathol. 10: 719-736 (1995); Kalff et al., Ann. Surg. 228: 652-663 (1998)). Most abundant of these are resident macrophages, which form an extensive network of cells from the esophagus to the colon, and which are poised to defend the gastrointestinal tract from potential injury and disease. Disturbances to the bowel during abdominal surgery activate this macrophage network, initiating a local molecular inflammatory response. The activated macrophages release pro-inflammatory cytokines (IL-6, IL-1β, TNFα) and chemokines (MCP-1) that suppress neuromuscular communication within the muscularis and induce the expression of adhesion molecules (ICAM-1, P-selectin) on the vascular endothelium (Kalff et al., J. Leukoc. Biol. 63: 683-691 (1998); Josephs et al., J. Surg. Res. 86: 50-54 (1999); Kalff et al., Gastroenterology 117: 378-387 (1999); Kalff et al., Gastroenterology 118: 316-327 (2000); Wehner et al., Surgery 137: 436-46 (2005)). This in turn leads to a cellular inflammatory response characterized by recruitment of leukocytes (monocytes, neutrophils, T-cells, mast cells) from the systemic circulation, where there is a positive correlation between the magnitude of the inflammatory cell infiltrate and the severity of ileus (Kalff et al., Surgery 126: 498-509 (1999)). Infiltrating leukocytes release additional cytokines as well as prostaglandins, nitric oxide, proteases and reactive oxygen species that further contribute to neuromuscular dysfunction (von Ritter et al., Gastroenterology 97: 605-609 (1989); Bielefeldt and Conklin, Dig. Dis. Sci. 42: 878-884 (1997)).

To date, there are few options available in the clinic for management of inflammatory ileus. Prokinetics such as cisapride and neostigmine have been shown to improve post-operative bowel motility (Shibata and Toyoda, Surg. Today 28: 787-791 (1998)). However, results are inconsistent and these drugs have an increased risk of adverse cardiovascular effects that have proven difficult to predict in terms of severity and patient susceptibility. COX-2 inhibitors have been shown in animal studies to be protective against postoperative dysmotility of the small bowel (Schwarz et al., Gastroenterology 121: 1354-1371 (2001)), but had little effect on colonic dysmotility (Turler et al., Anal. Surg., 231(1): 56-66 (2002)). Phase I clinical trials in humans were completed comparing celecoxib and rofecoxib (Bouras et al., Neurogastroenterol. Motil. 16: 729-735 (2004)), and neither agent was found to improve post-operative motility.

The rapid return to oral feeding after surgery has been promoted as a means to stimulate normal hormonal regulation of motility patterns. This was found to hasten the return of bowel function and to improve comfort in a subset of patients when used as part of a multi-modal approach to bowel rehabilitation (Holte & Kehlet, Minerva. Anestesiol., 68(4): 152-156 (2002)). However, this treatment did not result in a significant reduction in the length of hospital stay. Furthermore, adequate stimulation of hormonal patterns requires a threshold caloric load that many patients are unable to tolerate.

One of the most common factors contributing to the development of prolonged ileus is the administration of opioid analgesics for postoperative pain relief. Opioids exert their analgesic effects by interacting with one or more of three receptor subtypes present on neurons in the pain processing centers of the brain. Most current opioid analgesics, such as morphine, work primarily by activating μ-(mu) and δ (delta)-opioid receptors. However, these same receptors are also expressed on the neurons within the gastrointestinal tract that control bowel motility. Activation of the receptors, whether in the presence or absence of inflammatory ileus, significantly suppresses gastrointestinal contractile function, causing bowel stasis and constipation. Adalor Corporation has conducted Phase I and II clinical trials using Alvimopan, a peripherally restricted and selective μ-OR antagonist that does not cross the blood-brain barrier. When given in conjunction with opioid analgesics, Alvimopan prevented opioid-induced suppression of intestinal motility (Gonenne et al., Clin. Gastroenterol. Hepatol. 3: 784-791 (2005)). When compared with placebo, Alvimopan was found to hasten return of bowel function and to shorten hospital stay in patients who were experiencing mild to moderate postoperative ileus after having undergone abdominal surgery (Viscusi et al., Surg. Endosc. 20: 64-70 (2006)). Alvimopan does not alter inflammation.

To date, there are no safe and reliable treatment options available for the treatment of inflammatory ileus. The most effective remedies currently available are supportive in nature or ameliorate the compounding effects of opioid analgesia. They do not address inflammation as the underlying cause of ileus. Therefore, a significant unmet medical need remains.

SUMMARY OF THE INVENTION

Figure 1:
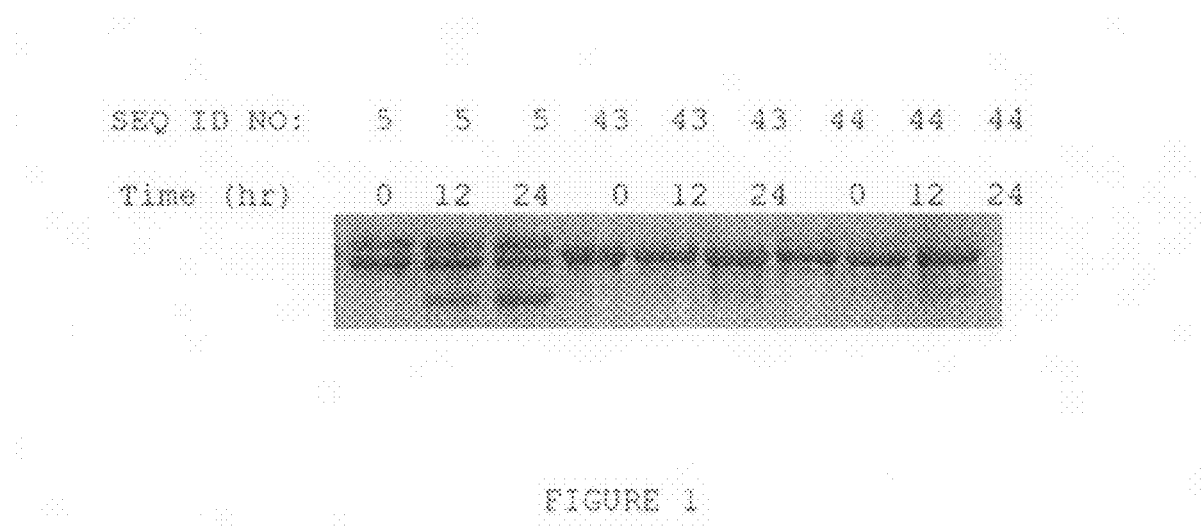
FIG. 1 shows the image of a SDS-PAGE gel of GLP-2 mimetibody Pro substitution variants (SEQ ID NOs: 43 and 44) after incubation with U937 cell lysate.

One aspect of the invention is a mimetibody having the generic formula (II):

(GLP2RAg-Lk-V2-Hg—$C_H2$-$C_H3$)$_{(t)}$     (II)

where GLP2RAg is a mammalian GLP-2R agonist, Lk is a polypeptide or chemical linkage, V2 is a portion of a C-terminus of an immunoglobulin variable region, Hg is at least a portion of an immunoglobulin variable hinge region, $C_H2$ is an immunoglobulin heavy chain $C_H2$ constant region and $C_H3$ is an immunoglobulin heavy chain $C_H3$ constant region and t is independently an integer from 1 to 10.

Another aspect of the invention is a mimetibody comprising a polypeptide having the sequence shown in SEQ ID NO: 4, 5, 6, 7, 8, 9, 10, 11, 42, 43, 44, 45, 58, 59, 60, 61, 62, 63, 64, 65, 75, or 77.

Another aspect of the invention is a polynucleotide comprising a polynucleotide having the sequence shown in SEQ ID NO: 12, 13, 14, 15, 16, 17, 18, 46, 47, 48, 49, 66, 67, 68, 69, 70, 71, 72, 73, 76, or 78 or a complementary sequence.

Another aspect of the invention is a polynucleotide comprising a polynucleotide encoding the amino acid sequence shown in SEQ ID NO: 4, 5, 6, 7, 8, 9, 10, 11, 42, 43, 44, 45, 58, 59, 60, 61, 62, 63, 64, 65, 75, or 77.

Another aspect of the invention is a polypeptide comprising a polypeptide having the sequence shown in SEQ ID NO: 52, 54, 55 or 74.

Another aspect of the invention is a polynucleotide comprising a polynucleotide encoding the amino acid sequence shown in SEQ ID NO: 52, 54, 55, or 74.

Another aspect of the invention is a method of reducing the symptoms of, or treating a disorder characterized by injury and/or dysfunction of the intestinal mucosal epithelium, comprising administering a GLP-2 polypeptide composition or a GLP-2 mimetibody composition to a patient in need thereof.

Another aspect of the invention is a method of preventing, reducing the symptoms of, or treating inflammatory ileus, comprising administering a GLP-2 polypeptide composition or a GLP-2 mimetibody composition to a patient in need thereof.

DETAILED DESCRIPTION OF THE INVENTION

All publications, including but not limited to patents and patent applications, cited in this specification are herein incorporated by reference as though fully set forth. Single letter amino acid codes are used herein as understood by those skilled in the art. Numbering of amino acid residues in immunoglobulin constant regions is based on residue one being the N-terminal amino acid in a wild type IgG1 or IgG4 Fc domain.

The present invention provides protein constructs having the properties and activities of mammalian GLP-2. One embodiment of the invention is protein constructs that mimic different types of immunoglobulin molecules such as IgA, IgD, IgE, IgG, or IgM, and any subclass thereof, such as IgA1, IgA2, IgG1, IgG2, IgG3 or IgG4, or combinations thereof, hereinafter referred to as "GLP-2 mimetibodies" or simply "mimetibodies." Another embodiment of the invention is polypeptides that are variants of GLP-2 where the polypeptides have the properties and activities of the wild type molecule. The invention also provides nucleic acids encoding GLP-2 mimetibodies, polypeptides, vectors containing these nucleic acids, host cells, compositions and methods of making and using GLP-2 mimetibodies and polypeptides.

GLP-2 Mimetibodies, Polypeptides and Compositions

The present invention generally relates to mimetibody polypeptides having the generic formula (I):

(Pep-Lk-V2-Hg—$C_H2$-$C_H3$)$_{(t)}$     (I)

where Pep is a polypeptide having a desired biological property, Lk is a polypeptide or chemical linkage, V2 is a portion of a C-terminus of an immunoglobulin variable region, Hg is at least a portion of an immunoglobulin hinge region, $C_H2$ is an immunoglobulin heavy chain $C_H2$ constant region and $C_H3$ is an immunoglobulin heavy chain $C_H3$ constant region and t is independently an integer of 1 to 10.

More particularly, the present invention relates to GLP-2 mimetibody polypeptides that are capable of, upon binding, activating GLP-2R. The polypeptides have the generic formula (II):

(GLP2RAg-Lk-V2-Hg—$C_H2$-$C_H3$)$_{(t)}$     (II)

where GLP2RAg is a mammalian GLP-2R agonist, Lk is a polypeptide or chemical linkage, V2 is a portion of a C-terminus of an immunoglobulin variable region, Hg is at least a portion of an immunoglobulin hinge region, $C_H2$ is an immunoglobulin heavy chain $C_H2$ constant region and $C_H3$ is an immunoglobulin heavy chain $C_H3$ constant region and t is independently an integer of 1 to 10.

As used herein, "GLP-2R agonist" encompasses any molecule which, upon binding to, activates GLP-2R. GLP-2R agonists include wild-type mammalian GLP-2 and peptidic analogs of GLP-2. An exemplary wild-type GLP-2 peptide has the amino acid sequence shown in SEQ ID NO: 1. It is known that certain amino acid residues in naturally occurring GLP-2 can be substituted for other amino acid residues with the analogs maintaining the GLP-2R binding property of the wild-type GLP-2. For example, Ala2 of the wild-type human GLP-2 peptide can be substituted with Ser (A2S) or Gly (A2G). The resulting amino acid sequences are shown in SEQ ID NOs: 2 and 3, respectively.

In the present invention, novel analogs of wild-type human GLP-2 have been developed that function as GLP-2R agonists. Amino acid sequences of these analogs are shown in SEQ ID NOs: 50, 51, 52, 53, 54, 55, 56, 57, and 74 shown below (mutations designated against wild type GLP-2). These analogs are useful as GLP2RAg components of a mimetibody.

| SEQ ID NO: | Amino acid sequence | Mutations |
|---|---|---|
| 50 | HGDGSFSSDMSTILDNLAARDFINWLI QTKITD | A2G, D8S, E9D, N11S |
| 51 | HGDGSFSSDVSTILDNLAARDFINWLI QTKITD | A2G, D8S, E9D, M10V, N11S |
| 52 | HGDGSFSDEMNTYLDNLAARDFINWLI QTKITD | A2G, I13Y |
| 53 | HGDGSFSDEMNTILDCLAARDFINWLI QTKITD | A2G, N16G |
| 54 | HGDGSFSDEMNTILDNQAARDFINWLI QTKITD | A2G, L17Q |
| 55 | HGDGSFSDEMNTILDGQAARDFINWLI QTKITD | A2G, N16G, L17Q |
| 56 | HGDGSFSDEMNTILDNLAARDFIAWLI QTKITD | A2G, N24A |

-continued

| SEQ ID NO: | Amino acid sequence | Mutations |
|---|---|---|
| 57 | HGDGSFSDEMNTILDNLAARDFINWLV KGKITD | A2G, I27V, Q28K, T29G |
| 74 | HGDGSFSDEVNTILDNLAARDFINWLI QTKITD | A2G, M10V |

It has been observed that GLP-2 peptides can self-associate and pose a problem for development and manufacture of a homogeneous therapeutic candidate. See US Patent Application Publication No. 20040122210 A1. As described in the Examples below, the polypeptides having the amino acid sequences shown in SEQ ID NOs: 52, 54, 55 and 74 were designed to be monomeric at pH 7.5 and have reduced helical propensities. Accordingly, these human GLP-2 peptide analogs would be particularly useful in a mimetibody construct or as a naked therapeutic peptide.

In the mimetibodies of the invention, the linker portion (Lk) provides structural flexibility by allowing the mimetibody to have alternative orientations and binding properties. Exemplary linkers include non-peptide chemical linkages or one to 20 amino acids linked by peptide bonds, wherein the amino acids are selected from the 20 naturally occurring amino acids. The linker portion can include a majority of amino acids that are sterically unhindered, such as glycine, alanine and serine and include GS, GGGS (SEQ ID NO: 19), GSGGGS (SEQ ID NO: 20), and polymers or combinations thereof. Other exemplary linkers within the scope of the invention may be longer than 20 residues and may include residues other than glycine, alanine and serine.

In the mimetibodies of the invention, V2 is a portion of a C-terminal domain of an immunoglobulin variable region such as a heavy chain variable region. An exemplary V2 amino acid sequence is GTLVTVSS (SEQ ID NO: 21).

It has been shown that O-glycosylation can occur at the two Tyr residues in the V2 region, although the extent of glycosylation is highly dependent on the host cell line and may also be influenced by culture conditions. O-glycans may act to block aggregation and proteolysis, resulting in greater in vivo stability. However, it may be desirable to abrogate the O-glycosylation because of heterogeneity and poor reproducibility. Accordingly, an alternative exemplary V2 amino acid sequence is GALVAVSS (SEQ ID NO: 22).

In the mimetibodies of the invention, Hg is a portion of the hinge domain of an immunoglobulin variable region such as a heavy chain variable region. Exemplary Hg amino acid sequences include EPKSCDKTHTCPPCP (SEQ ID NO: 23), EPKSADKTHTCPPCP (SEQ ID NO: 24), ESKYGPPCP-SCP (SEQ ID NO: 25), ESKYGPPCPPCP (SEQ ID NO: 26) and CPPCP (SEQ ID NO: 27).

In the mimetibodies of the invention, $C_H2$ is an immunoglobulin heavy chain $C_H2$ constant region. Exemplary $C_H2$ amino acid sequences include:

(SEQ ID NO: 28)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAK, (SEQ ID NO: 29)
APEAAGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAK, (SEQ ID NO: 30)
APEFLGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPS

SIEKTISKAK and (SEQ ID NO: 31)
APEAAGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPS

SIEKTISKAK.

In the mimetibodies of the invention, $C_H3$ is an immunoglobulin heavy chain $C_H3$ constant region. Exemplary $C_H3$ amino acid sequences include: GQPREPQVYTLPPSRDELTKNQVSLT-CLVKGFYPSDIAVEWESNGQPENNYKTTPPVLDSD GSFFLYSKLTVDKSRWQQGNVFSCSVM-HEALHNHYTQKSLSLSPGK (SEQ ID NO: 32) and GQPREPQVYTLPPSQEEMTKNQVSLT-CLVKGFYPSDIAVEWESNGQPENNYKTTPPVLDSD GSFFLYSRLTVDKSRWQEGNVFSCSVM-HEALHNHYTQKSLSLSLGK (SEQ ID NO: 33). It will be recognized by those skilled in the art that the $C_H3$ region of the mimetibodies of the invention may have its C-terminal amino acid cleaved off when expressed in certain recombinant systems.

In the mimetibodies of the invention, the FcRn scavenger receptor binding site of the immunoglobulin molecules is preserved at the junction of the $C_H2$ and $C_H3$ region. Since FcRn binding enables the return of pinocytosed immunoglobulin back to the extracellular space, it is expected that the half-life of GLP-2 mimetibodies will be significantly extended relative to GLP-2 peptides.

In one embodiment of the mimetibodies of the invention, the monomeric structure (GLP2-Lk-V2-Hg—$C_H2$-$C_H3$) can be linked to other monomers non-covalently or by covalent linkage, such as, but not limited to, a Cys-Cys disulfide bond.

IgG1 and IgG4 subclasses differ in the number of cysteines in the hinge region. Like the IgG1 subclass, there are two cysteines in the IgG4 hinge that participate in the disulfide bonding between heavy chains. However, the cysteine in IgG1 hinge that is normally involved in disulfide bonding to the light chain is absent in the IgG4 hinge. Therefore, the IgG4 hinge is less flexible than the IgG1 hinge.

In addition, the two isotypes differ in their ability to mediate complement dependent cytotoxicity (CDC) and antibody-dependent cellular cytotoxicity (ADCC). CDC is the lysing of a target in the presence of complement. The complement activation pathway is initiated by the binding of the first component of the complement system (C1q) to a molecule complexed with a cognate antigen. IgG1 is a strong inducer of the complement cascade and subsequent CDC activity, while IgG4 has little complement-inducing activity.

ADCC is a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The IgG1 subclass binds with high affinity to the Fc receptor and contributes to ADCC while IgG4 binds only weakly. The relative inability of IgG4 to activate effector functions is desirable since delivery of the mimetibody to cells without cell killing is possible.

Furthermore, the binding site for the FcRn scavenger receptor is present in IgG4 and IgG1 isotypes and both have similar binding characteristics. Therefore, the pharmacokinetics of the IgG1 and IgG4 mimetibodies of the invention are expected to be similar.

The hinge-$C_H2$-$C_H3$ portion of the immunoglobulin region (Hg—$C_H2$-$C_H3$) may also be extensively modified to form variants in accordance with the invention. For example, one or more native sites that provide structural features or functional activity not required by the mimetibody molecules could be removed. These sites may be removed by, for example, substituting or deleting residues, inserting residues into the site, or truncating portions containing the site. Exemplary Hg—$C_H2$-$C_H3$ variants are discussed below.

1. Sites involved in disulfide bond formation can be removed by deletion or substitution with other amino acids in the mimetibodies of the invention. Typically, the cysteine residues present in these motifs are removed or substituted. Removal of these sites may avoid disulfide bonding with other cysteine-containing proteins present in the mimetibody-producing host cell or intra-heavy chain disulfide bonding in IgG4-based constructs while still allowing for a dimeric CH3-CH2-hinge domain that is held together non-covalently.

Most IgG type antibodies, such as IgG1, are homodimeric molecules made up of two identical heavy (H) chains and two identical light (L) chains, typically abbreviated $H_2L_2$. Thus, these molecules are generally bivalent with respect to antigen binding, i.e., both antigen binding (Fab) arms of the IgG molecule have identical binding specificity.

IgG4 isotype heavy chains contain a CPSC (SEQ ID NO: 34) motif in their hinge regions capable of forming either inter- or intra-heavy chain disulfide bonds, i.e., the two Cys residues in the CPSC motif may disulfide bond with the corresponding Cys residues in the other H chain (inter) or the two Cys residues within a given CPSC motif may disulfide bond with each other (intra). It is believed that in vivo isomerase enzymes are capable of converting inter-heavy chain bonds of IgG4 molecules to intra-heavy chain bonds and vice versa (Aalberse and Schuurman, *Immunology* 105, 9-19 (2002)). Accordingly, since the HL pairs in those IgG4 molecules with intra-heavy chain bonds in the hinge region are not covalently associated with each other, they may dissociate into HL monomers that then reassociate with HL monomers derived from other IgG4 molecules forming bispecific, heterodimeric IgG4 molecules. In a bispecific IgG antibody the two Fabs of the antibody molecule differ in the epitopes that they bind. Substituting Ser228 in the hinge region of IgG4 with Pro results in "IgG1-like behavior," i.e., the molecules form stable disulfide bonds between heavy chains and therefore, are not susceptible to HL exchange with other IgG4 molecules.

2. The H—$C_H2$-$C_H3$ can be modified to make the mimetibodies of the invention more compatible with a selected host cell. For example, when a mimetibody of the invention is expressed recombinantly in a bacterial cell such as *E. coli*, the Pro-Ala sequence in the hinge may be removed to prevent digestion by the *E coli* enzyme proline iminopeptidase.

3. A portion of the hinge region can be deleted or substituted with other amino acids in the mimetibodies of the invention to prevent heterogeneity in the products expressed in a selected host cell.

4. One or more glycosylation sites can be removed in the mimetibodies of the invention. Residues that are typically glycosylated (e.g., Asn) may confer an Fc-dependent, cell-mediated cytolytic activity to the mimetibody. Such residues may be deleted or substituted with residues that are not glycosylated such as Ala.

5. Sites involved in interaction with complement, such as the Clq binding site, are removed in the mimetibodies of the invention.

6. Sites can be removed that affect binding to Fc receptors other than an FcRn salvage receptor in the mimetibodies of the invention. For example, the Fc receptors involved in ADCC activity can be removed in the mimetibodies of the invention. For example, mutation of Leu234/Leu235 in the hinge region of IgG1 to L234A/L235A or Phe234/Leu235 in the hinge region of IgG4 to P234A/L235A minimizes FcR binding and reduces the ability of the immunoglobulin to mediate complement dependent cytotoxicity and ADCC.

One embodiment of the present invention is a GLP-2 mimetibody according to formula (II) where the Hg—$C_H2$-$C_H3$ is from the IgG4 subclass and contains a Ser228Pro (S228P) substitution and P234A/L235A mutations. The complete polypeptide sequences of exemplary GLP-2 mimetibodies having these mutations and A2S and A2G in GLP-2 peptide sequence are shown respectively in SEQ ID NOs: 4 and 5. These sequences contain all of the domains of the mimetibody construct, namely the GLP2RAg-Lk-V2-Hg—$C_H2$-$C_H3$ domains. These mimetibody constructs are expected to be a homogeneous and stable population that does not trigger FcR-mediated effector functions. The substitution and mutations shown here are exemplary; Hg—$C_H2$-$C_H3$ domains within the scope of this invention may include other substitutions, mutations and/or deletions.

The partial polypeptide sequences of other exemplary A2G based GLP-2 mimetibodies of the invention with variable linker lengths are shown in SEQ ID NOs: 6, 7, 8, 9, 10 and 11. These sequences show all domains with the exception of the $C_H2$ and $C_H3$ domains. It will be understood by those skilled in the art that a $C_H2$ and $C_H3$ domain would be contained in a functional mimetibody.

The partial polypeptide sequences of other exemplary GLP-2 mimetibodies of the invention based on the GLP-2 analogs having the amino acid sequences shown in SEQ ID NOs: 50, 51, 52, 53, 54, 55, 56, and 57 are shown in SEQ ID NOs: 58, 59, 60, 61, 62, 63, 64, and 65, respectively. These sequences show all domains with the exception of the $C_H2$ and $C_H3$ domains. It will be understood by those skilled in the art that a $C_H2$ and $C_H3$ domain would be contained in a functional mimetibody.

The present invention includes GLP-2 mimetibodies that are capable of, upon binding, activating GLP-2R. The mimetibodies of the present invention can bind GLP-2R with a wide range of affinities. The affinity of a GLP-2 mimetibody for GLP-2R can be determined experimentally using any suitable method, for example, methods using Biacore or KinExA instrumentation, ELISA and competitive binding assays.

The GLP-2 mimetibodies and polypeptides of the present invention are useful in treating disorders or symptoms characterized by inflammation, injury and/or dysfunction of the intestinal mucosal epithelium. Effects of GLP-2 are also noted in bone formation and maintenance, and in central nervous system mediated disorders due to its role as a central satiety factor. Diseases or symptoms that can be treated using GLP-2 mimetibodies or polypeptides of the invention include, but are not limited to, GI diseases, including SBS, inflammatory bowel disease (IBD), Crohn's disease, colitis, pancreatitis, ileitis, inflammatory ileus (both postoperative and from other causes), mucositis associated with cancer chemotherapy and/or radiotherapy, intestinal atrophy caused by total parenteral nutrition or ischemia, bone related disorders such as osteoporosis, nutrient related disorders including obesity, and pediatric GI disorders including intestinal failure due to necrotizing enterocolitis in newborn infants. GLP-2 mimetibodies or polypeptides of the present invention can also be used to prevent, reduce the symptoms of, and treat inflammatory ileus.

Accordingly, another aspect of the present invention is pharmaceutical compositions comprising at least one GLP-2 mimetibody or polypeptide of the invention and a pharmaceutically acceptable carrier or diluent known in the art. The carrier or diluent can be a solution, suspension, emulsion, colloid or powder.

A GLP-2 mimetibody or polypeptide of the invention is formulated as a pharmaceutical composition in a therapeutically or prophylactically effective amount. The term "effective amount" generally refers to the quantities of mimetibody or polypeptide necessary for effective therapy, i.e., the partial or complete alleviation of the symptom or disorder for which treatment was sought. Included within the definition of effective therapy are prophylactic treatments intended to reduce the likelihood of onset of the above-described symptoms or disorders.

The composition can optionally comprise at least one further compound, protein or composition useful for treating the disease states discussed herein. For example, the mimetibodies or polypeptides of the invention can be used in combination with glutamine or other nutritional supplements are contemplated to increase body weight, aid in intestinal healing or improve nutrient absorption. Further, combination with anti-inflammatory agents are also contemplated. The term "in combination with" as used herein and in the claims means that the described agents can be administered to a mammal together in a mixture, concurrently as single agents or sequentially as single agents in any order.

Nucleic Acids, Vectors and Cell Lines

Another aspect of the present invention is isolated nucleic acid molecules comprising, complementary to or having significant identity with a polynucleotide encoding at least one GLP-2 mimetibody or polypeptide of the invention. Other aspects of the present invention include recombinant vectors comprising at least one isolated GLP-2 mimetibody or polypeptide of the invention encoding nucleic acid molecule and cell lines and organisms that are capable of expressing the nucleic acid molecules. The nucleic acids, expression vectors and cell lines may generally be used to produce the mimetibody of the invention.

In one embodiment, the nucleic acid compositions of the invention encode polypeptides having amino acid sequences identical to or substantially homologous to any one of SEQ ID NOs: 4, 5, 6, 7, 8, 9, 10, 11, 42, 43, 44, 45, 58, 59, 60, 61, 62, 63, 64, 65, 74, 75, and 77. Exemplary nucleic acid sequences that encode the polypeptide sequences shown in SEQ ID NO: 5, 6, 7, 8, 9, 10, 11, 42, 43, 44, 45, 58, 59, 60, 61, 62, 63, 64, 65, 75, and 77 are shown in SEQ ID NO: 12, 13, 14, 15, 16, 17, 18, 46, 47, 48, 49, 66, 67, 68, 69, 70, 71, 72, 73, 76, and 78, respectively. Also provided are allelic variations of the above-described nucleic acids.

Typically, the nucleic acids of the present invention are used in expression vectors for the preparation of the GLP-2 mimetibody or polypeptides of the invention. Vectors within the scope of the invention provide necessary elements for eukaryotic expression, including viral promoter driven vectors, such as CMV promoter driven vectors, e.g., pcDNA3.1, pCEP4 and their derivatives, Baculovirus expression vectors, Drosophila expression vectors and expression vectors that are driven by mammalian gene promoters, such as human Ig gene promoters. Other examples include prokaryotic expression vectors, such as T7 promoter driven vectors, e.g., pET41, lactose promoter driven vectors and arabinose gene promoter driven vectors.

The present invention also relates to cell lines expressing GLP-2 mimetibodies or polypeptides of the invention. The host cells can be prokaryotic or eukaryotic cells. Exemplary eukaryotic cells are mammalian cells, such as but not limited to, COS-1, COS-7, HEK293, BHK21, CHO, BSC-1, HepG2, 653, SP2/0, NS0, 293, HeLa, myeloma, lymphoma cells, or any derivative thereof. Most preferably, the host cells are HEK293, NS0, SP2/0 or CHO cells. The cell lines of the present invention may stably express at least one GLP-2 mimetibody. The cell lines may be generated by stable or transient transfection procedures that are well known in the art.

The present invention further provides methods for expressing at least one GLP-2 mimetibody or polypeptide comprising culturing the cell lines under conditions wherein the GLP-2 mimetibody or polypeptide is expressed in detectable or recoverable amounts. The present invention also provides methods for generating at least one GLP-2 mimetibody or polypeptide comprising translating the GLP-2 mimetibody or polypeptide encoding nucleic acids under conditions in vitro or in situ, such that the GLP-2 mimetibody or polypeptide is expressed in detectable or recoverable amounts. The present invention also encompasses GLP-2 mimetibodies or polypeptides produced by the above methods.

A GLP-2 mimetibody can be recovered and purified by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylatpatite chromatography and lectin chromatography. Reversed phase high performance liquid chroatography (RP-HPLC) can also be employed for purification.

Alternatively, a GLP-2 derived polypeptide of the invention can be prepared by chemical synthesis techniques well known to those skilled in the art. Polypeptides of the invention produced by either recombinant or chemical methods can be recovered and purified by methods well known to those skilled in the art.

Methods of Use

The GLP-2 mimetibodies or polypeptides are useful as, inter alia, research reagents and therapeutic agents. In one aspect, the present invention relates to a method of modifying the biological activities of GLP-2 comprising providing at least one GLP-2 mimetibody or polypeptide to a mammal in need thereof. The GLP-2 mimetibody or polypeptide may activate cell signaling cascades through GLP-2R. In particular, the GLP-2 mimetibody or polypeptide may function as an agonist of GLP-2R. The term "agonist" is used in the broadest sense and includes a molecule that is capable of, directly or indirectly, partially or fully activating, increasing or promoting one or more biological activities of GLP-2R.

The present invention also provides methods for reducing the symptoms of, or treating at least one GLP-2 related condition or disease comprising administering a therapeutically effective amount of at least one GLP-2 mimetibody or polypeptide pharmaceutical composition to a patient in need thereof. The conditions and diseases suitable for treatment using the methods of the present invention include but are not limited to GI diseases, including SBS, Crohn's disease, and pediatric GI disorders, mucositis associated with cancer che motherapy, IBD, inflammatory ileus, and other diseases and conditions described above.

GLP-2 interacts preferentially with GLP-2R found primarily on neurons of the enteric nervous system, and on GLP-2 containing enteroendocrine cells (Guan et al., Gastroenterology 130: 150-164 (2006)). One of the primary functions of GLP-2 is to promote columnar cell proliferation in the villus crypts where it enhances epithelial cell turnover and mucosal wound healing (Bulut et al., Regul. Pept. 121: 137-43 (2004)), enhances mucosal barrier function (Benjamin et al., Gut 47: 112-119 (2000)), and inhibits cell death by apoptosis (Brubaker and Drucker, Endocrinology 145: 2653-2659 (2004)). These effects have been shown to be neurally dependent as GLP-2R is not expressed in crypt columnar epithelial cells (Bjerknes and Cheng, Proc. Natl. Acad. Sci. U.S.A. 98: 12497-12502 (2001)). The presence of GLP-2R on enteric neurons suggests that GLP-2 may modify motility as well as neuro-immune interactions that play a role in intestinal inflammation.

Accordingly, the present invention further provides methods of preventing, reducing the symptoms of, or treating inflammatory ileus, comprising administering a GLP-2 polypeptide composition or a GLP-2 mimetibody composition to a patient in need thereof. As used herein, "inflammatory ileus" can be ileus of any portion of the gastrointestinal tract, e.g., the stomach, small intestine and/or the colon. In addition, "inflammatory ileus" can result from any factor that causes ileus, e.g., surgery, including abdominal surgery such as transplantation surgery or abdominal surgery other than transplantation surgery, bowel surgery such as bowel resection, and orthopedic surgery; traumatic injury, e.g., falls, car accident, personal assault, or any sequelae resulting from traumatic injury, e.g. limb fractures, rib fractures, fractures of the spine, thoracic lesions, ischaemia, retroperitoneal hematoma; intraperitoneal inflammation, e.g., intraabdominal sepsis, acute appendicitis, cholecystitis, pancreatitis, ureteric colic, basal pneumonia; myocardial infarction; metabolic disturbances; or any combination thereof.

As described above, the GLP-2 mimetibody or polypeptide pharmaceutical composition comprises an effective amount of at least one GLP-2 mimetibody or polypeptide and a pharmaceutically acceptable carrier or diluent. The effective amount for a given therapy, whether curative or preventative, will generally depend upon may different factors, including means of administration, target site and other medicants administered. Thus, treatment doses will need to be titrated to optimize safety and efficacy.

The methods of the present invention can optionally further comprise co-administration or combination therapies with any standard therapy used to treat the diseases listed above.

The mode of administration can be any suitable route to deliver the pharmaceutically effective amount of GLP-2 mimetibody or polypeptide of the present invention to a host. For example, the GLP-2 mimetibody or polypeptide can be delivered via parenteral administration, such as subcutaneous, intramuscular, intradermal, intravenous or intranasal administration, or any other means known in the art.

The present invention is further described with reference to the following examples. These examples are merely to illustrate aspects of the present invention and are not intended as limitations of this invention.

EXAMPLE 1

Cloning, Expression and Purification of GLP-2 Mimetibodies in Mammalian Cells

Nucleic acid sequence encoding A2S GLP-2 was generated in a 2-step PCR amplification. The first round amplification was performed using forward primer 5'-CCAAAG TATACAGGCGCATAGCGATGGTTCTTTCTCTGATGAG ATGAACACCATTCTTG-3' (SEQ ID NO: 37) and reverse primer 5'-TTGGTCTGAATCAACCAGTTTATAAAGTCT CGAGCGGCAAGATTATCAAGAATGGTGTTCA TCTC-3' (SEQ ID NO: 38). The melting, annealing and extension temperature were set at 96° C., 48° C., and 72° C., respectively. Three cycles of reactions were carried out.

For the second round amplification, the forward primer included a NotI restriction enzyme recognition site and the reverse primers included a BamHI site. The sequence of the forward primer is 5'-TTTGCGGCCGCCCAAAGTATA-CAGGCG-3' (SEQ ID NO: 39) and reverse primer 5'-AAAG-GATCCGTCAGTGATTTGGTCTGAATCAACCAG-3' (SEQ ID NO: 40). The melting, annealing and extension temperature were set at 96° C., 48° C., and 60° C., respectively. Thirty cycles of reactions were carried out.

Nucleic acid sequence encoding A2G GLP-2 was generated in the same procedure except the forward primer used in the first round of amplification is 5'-CCAAAGTATACAG-GCGCATGGCGATGGTTCTTTCTCTGAT-GAGATGAACACCATTCTTG-3' (SEQ ID NO: 41).

The amplified PCR products (A2S and A2G GLP-2) were cloned into the NotI/BamHI sites of a CMV promoter driven, human IgG4 ΔCH1, Ser to Pro, Ala/Ala expression vector using standard cloning procedures.

The A2S and A2G GLP-2 IgG4 mimetibodies were transiently expressed in HEK 293E cells and purified from the conditioned media using protein A affinity chromatography according to standard procedures. The eluted material from the protein A affinity column was further subjected to a size exclusion column for further purification.

The purified A2S and A2G GLP-2 mimetibodies were analyzed by SDS-polyacrylamide gel electrophoresis (SDS-PAGE) and size exclusion chromatography coupled to static light scattering analysis (SEC-SLS). The migration of the purified mimetibodies on SDS-PAGE under both reducing and non-reducing denaturing conditions was in the expected range. Analysis by SEC-SLS showed a protein with a molecular weight of approximately 123 KD corresponding to the dimer of the mimetibodies. Since the GLP-2 Mimetibodies migrate as a monomer on the SDS-PAGE gel, the dimerization is via non-covalent interactions.

EXAMPLE 2 cAMP Expression Assay

In order to evaluate the in vitro activities of the GLP-2 mimetibodies, a CAMP expression assay was developed. To achieve this goal, a clonal cell line expressing a mutated human GLP-2R was generated by transfecting HEK 293E cells. The mutated human GLP-2R differs from the wild-type human GLP-2R (SEQ ID NO: 35) at three amino acid positions within the C-terminal intracellular region (SEQ ID NO: 36). GLP-2 peptide stimulated cAMP expression in this cell line and the stimulation was specific, as a control peptide did not stimulate cAMP expression.

A2S and A2G IgG4 GLP-2 mimetibodies were compared with the corresponding GLP-2 peptides (A2S and A2G) for their ability to stimulate cAMP expression in the recombinant cell line. Briefly, cells were incubated with individual GLP-2 mimetibody or GLP-2 peptide for 30 minutes. The cAMP expression was quantitated using the cAMP Direct Screen System (Cat. No. CSD 200, Applied Biosystems, Bedford, Mass.). The $EC_{50}$ for A2S and A2G peptides are 0.5 nM and 0.8 nM, respectively; the $EC_{50}$ for A2S and A2G mimetibodies are 2.2 nM and 3.8 nM, respectively. Therefore, the potency of the GLP-2 mimetibodies in this assay was ~4-fold less than the peptide.

EXAMPLE 3

GLP-2 Mimetibody Variants

To investigate the effect of linker length on the GLP-2 mimetibody, different constructs with various linker lengths were generated. The sequences of the core region are shown below in Table 1.

These variants were expressed transiently in HEK 293 cells, purified and analyzed by SDS-PAGE. Analysis by SEC-SLS showed a peak with a molecular weight of 65-70 kDa corresponding to the monomer of the mimetibodies in addition to one corresponding to the dimer of the mimetibodies. It was observed that the longer the linker length, the higher the proportion of the monomer population.

Linker length and V2 region variants were tested in the cAMP expression assay described in Example 2. The data demonstrated that the activities of the GLP-2 mimetibodies, as measured by $EC_{50}$, directly correlated with the linker length, i.e., mimetibodies with longer linkers have higher activity (Table 1).

TABLE 1

Core amino acid sequences and $EC_{50}$ of GLP2 mimetibodies with variable linker length.

| SEQ ID NO: | Amino acid sequence | $EC_{50}$ (nM) |
|---|---|---|
| 5* | HGDG3F3DEMNTILDNLAARDFINWLIQTKITDG3GGG3 GTLVTVS3ESKYGPPCPPCP | 5.1 |
| 6 | HGDGSFSDEMNTILDNLAARDFINWLIQTKITDGGGGSC PPCP | 40 |
| 7 | HGDGSFSDEMNTILDNLAARDFINWLIQTKITDGGGGSG GGGSCPPCP | 22.5 |
| 8 | HGDGSFSDEMNTILDNLAARDFINWLIQTKITDGGGGSG GGGSGGGGSCPPCP | 12.7 |
| 9 | HGDGSFSDEMNTILDNLAARDFINWLIQTKITDGGGGSG GGGSGGGGSGGGGSCPPCP | 4.6 |
| 10 | HGDGSFSDEMNTILDNLAARDFINWLIQTKITDGGGGSG GGGSGGGGSGGGGSGGGGSCPPCP | 2.1 |
| 11 | HGDGSFSDEMNTILDNLAARDFINWLIQTKITDGSGGGS GALVAVSSESLYGPPCPPCP | 3.1 |

* Only amino acid numbers 1-59 Of SEQ ID NO: 5 is shown in the table.
** SEQ ID NO: 11 shows a V2 region variant.

In order to increase the stability of GLP-2 mimetibodies, a series of variants were constructed in which the amino acid residues at the proteolytic cleavage sensitive sites in the V2 or Hg region were substituted with Pro. The core region sequences of the GLP-2 mimetibody variants are shown below in Table 2.

TABLE 2

Core amino acid sequences and $EC_{50}$ of GLP-2 mimetibodies with Pro substitution.

| SEQ ID NO: | Amino acid sequence | $EC_{50}$ (nM) |
|---|---|---|
| 42 | HGDGSFSDEMNTILDNLAARDFINWLIQTKITDGSGGGS GALVPVSSESKYGPPCPPCP | 3.6 |
| 43 | HGDGSFSDEMNTILDNLAARDFINWLIQTKITDGSGGGS GALVAVPSESKYGPPCPPCP | 4.8 |
| 44 | HGDGSFSDEMNTILDNLAARDFINWLIQTKITDGSGGGS GALVAVSPESKYGPPCPPCP | 7.7 |
| 45 | HGDGSFSDEMNTILDNLAARDFINWLIQTKITDGSGGGS GALVAVSSESKPGPPCPPCP | 5.8 |

The Pro substitution variants were expressed transiently in HEK 293 cells, purified and analyzed by SDS-PAGE. The data from the cAMP expression assay demonstrated that the activities of these GLP-2 mimetibody variants, as measured by $EC_{50}$, are comparable to that of the A2G GLP-2 mimetibody (SEQ ID NO: 5).

The purified Pro substitution variants were incubated with U937 cell lysate in the presence of CompleteMini protease inhibitor tablets (Cat. No. 1 836 153, Roche Applied Science, Indianapolis, Ind.) for 0, 12, or 24 hours. Afterwards, GLP-2 mimetibody variants were purified using Protein A beads and resolved on a SDS-PAGE gel. As shown in FIG. 1, in comparison with the A2G GLP-2 mimetibody (SEQ ID NO: 5), there was less degradation in Pro substitution variants (SEQ ID NO: 43 or 44) in the 24 hour test period. In conclusion, the Pro substitution variants are more resistant to proteolysis in vitro.

EXAMPLE 4

GLP-2 Mimetibody Stimulates the Mucosal Weight Gain in Small Intestine

To demonstrate the in vivo activities of the GLP-2 mimetibodies, CD1 mice were injected with the GLP-2 mimetibodies and endpoints within the small intestine were evaluated. Briefly, female CD1 mice were given daily subcutaneous injections of A2G GLP-2 peptide (SEQ ID NO: 3), A2G GLP-2 IgG4 mimetibody (SEQ ID NO: 5), or control mimetibody for 10 days. Afterwards, the mice were euthanized and the small intestines were removed, flushed with saline, and processed as described below.

Specifically, 4 cm sections were harvested: (1) immediately distal to the pylorus (duodenum), (2) starting 2 cm distal of the ligament of Treitz (jejunum), and (3) immediately proximal to the cecum (ileum). The remaining small intestine from ~6 cm distal of the ligament of Treitz to 4 cm proximal to the cecum was used to prepare mucosal scrapings. From the proximal and distal ends of the remnant, an equal distance was removed until a 15 cm section remained, the remnant was cut longitudinally, rinsed, and the mucosal layer was removed using the short end of a glass microscope slide. The wet weight of the intact intestinal segments and mucosa was measured.

Figure 2:
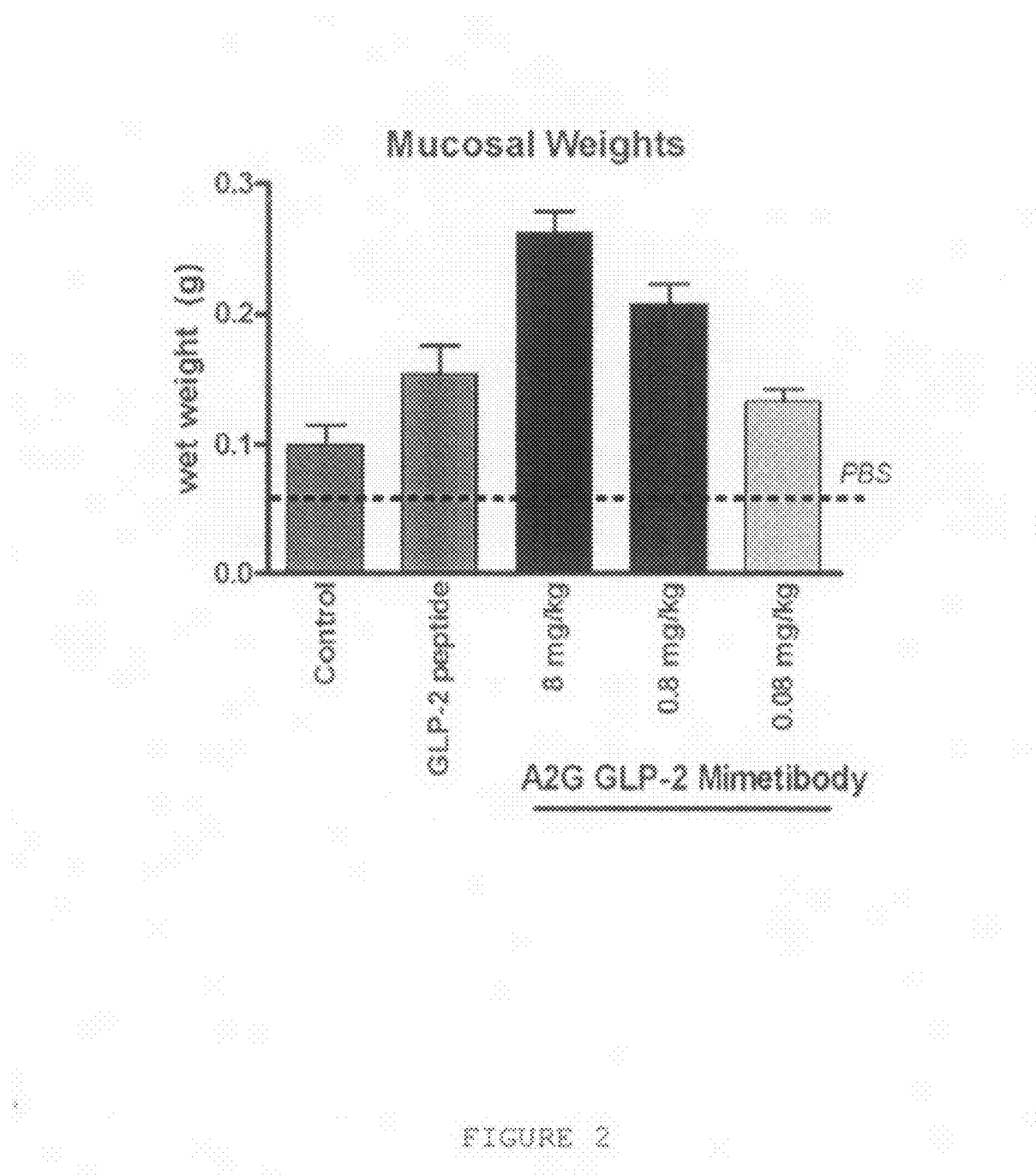
FIG. 2 shows a dose-dependent increase of the wet weight of mucosal scrapings from mice treated with A2G GLP-2 mimetibody.

The weight of the mucosal scrapings taken from the 15 cm segment between jejunum and ileum from different mice is shown in FIG. 2. For mice injected with A2G GLP-2 mimetibody, a dose dependant increase in mucosal wet weight was observed. At 0.8 and 8 mg/kg (0.26 and 2.6 nmole, respectively), the increase was statistically significant comparing with the control mimetibody (p<0.0001 and p<0.0004, respectively).

A statistically significant increase (p<0.0001) was also seen in mice injected with the A2G GLP-2 peptide at 2.5 mg/kg (13.3 nmole). In comparison, the A2G GLP-2 mimetibody is effective in vivo at a 50-fold lower dose than the A2G GLP-2 peptide (on a molar basis).

EXAMPLE 5

Pharmacokinetics of GLP-2 Mimetibody

To measure the pharmacokinetics of GLP-2 mimetibodies, CD1 mice were intravenously or subcutaneously dosed with 3 mg/kg of the A2G GLP-2 mimetibody (SEQ ID NO: 5). Blood was collected at different time points into citrate buffer containing protease inhibitors to minimize the possibility of ex vivo degradation and plasma was separated by centrifugation.

A time resolved fluorescence (TRF) assay was used to measure active mimetibody. Active mimetibody reflects the intact N-terminus of the peptide still attached to the Fc region of the mimetibody.

Based on the TRF experiments, the calculated half-life of the A2G GLP-2 mimetibody in mice was 26.5 hours. In contrast, the reported half-life of GLP-2 peptide in humans is 7.2+/−2 minutes (Hartmann et al., J. Clin. Endocrinol. Metab. 85: 2884-2888 (2000)). Therefore, the half-life of A2G GLP-2 mimetibody is more than 200-fold higher than that of the GLP-2 peptide.

In a similar experiment, cynomolgus monkeys were intravenously dosed with 1 mg/kg of the A2G GLP-2 mimetibody. Based on the TRF data, the calculated half-life of the A2G GLP-2 mimetibody in cynomolgus monkeys was 4.8 days.

EXAMPLE 6

Pharmacodynamics of GLP-2 Mimetibody

Based on its extended pharmacokinetics, the GLP-2 mimetibody is expected to have a longer duration of response. To evaluate the pharmacodynamics of the A2G GLP-2 mimetibody, mice were dosed daily, every other day, weekly, or once only at the start of the study. To control for animal handling, on days that the mice did not receive A2G GLP-2 mimetibody, they were injected with the negative control mimetibody, i.e., the mimetibody immunoglobulin scaffold without the GLP-2 peptide. The doses of the A2G GLP-2 mimetibody and the negative control were 4 mg/kg (1.3 nmoles/kg) for all groups. The duration of the study was 11 days and tissue was processed as described in Example 4.

Mice dosed with the A2G GLP-2 mimetibody once per week had a significantly increased mucosal weight compared to control mimetibody. The difference was more pronounced when the A2G GLP-2 mimetibody was administered every day, or every other day. Similar pattern was observed regarding the small intestinal section wet weight. In both the duodenum and jejunum, a significant increase in weight over the control mimetibody was seen with all regimens except for the single dose experiment.

EXAMPLE 7

Mutations in GLP-2 Prevent Peptide Dimerization

Wild-type GLP-2 peptide (SEQ ID NO: 1) dimerizes at high concentration. For example, in PBS (pH 7.5), GLP-2 exists as a monomer at 0.4 mg/mL but as a mixture of monomers (about 20%) and reversibly self-associated dimer (about 80%) at 2 mg/mL (data not shown). The self-association poses a challenge to the development and manufacturing of a homogeneous therapeutic.

Peptide analogs (SEQ ID NOs: 52, 54, 55, and 74) were designed that retain wild-type GLP-2 biological activity and exist as a monomer at high concentration. GLP-2(A2G, L17Q) (SEQ ID NO: 54) and GLP-2(A2G, N16G, L17Q) (SEQ ID NO: 55) were synthesized and purified to >95% purity. Peptides GLP-2 (SEQ ID NO: 1), GLP-2(A2G) (SEQ ID NO: 3), and GLP-1 (SEQ ID NO: 79) were included as controls in the characterization of the analogs.

Solution molecular weight of the peptides was measured by SEC-SLS. Briefly, peptide solutions in PBS (pH 7.5) at 0.4 to 2.0 mg/mL were fractionated over a Superdex peptide column (Amersham Pharmacia). The eluted peaks were monitored by static light scattering at 690 nm and solution molecular weight was determined at UV 280 nm using the Astra software package (Wyatt Inc.).

At 1 mg/ml, GLP-1 eluted as a single peak with molecular weight within the expected monomer size. GLP-2 and GLP-2(A2G) displayed similar distributions of overlapping dimer and monomer peaks. Both analog peptides GLP-2(A2G, L17Q) and GLP-2(A2G, N16G, L17Q) eluted as single peaks with molecular weight consistent with mainly monomeric peptide.

The secondary structures of tested peptides were determined using 0.2 mg/mL peptide solutions in PBS. Briefly, CD spectra were collected in triplicate at 1 nm intervals at 25° C. in 0.1 cm path length cell. Secondary structures were determined by fitting of the CD spectra using CD spectra software (CD Spectra Deconvolution software 2.1). All tested peptides contained peaks corresponding to the presence of alpha helices. However, helix content in the analog peptides GLP-2 (A2G, L17Q) and GLP-2(A2G, N16G, L17Q) was ~17%, similar to that of GLP-1, and lower than that of GLP-2 and GLP-2(A2G) (Table 3).

TABLE 3

Percentage of helical and random coil structure in GLP peptides

| Structure | GLP-2 | GLP-2 (A2G) | GLP-2 (A2G, L17Q) | GLP-2 (A2G, N16G, L17Q) | GLP-1 |
|---|---|---|---|---|---|
| Helix | 19.6% | 20.7% | 16.9% | 17.0% | 16.8% |
| Random coil | 37.9% | 37.1% | 41.8% | 41.4% | 41.9% |

In addition, trifluoroethanol (TFE) is known to induce helix formation in peptides (Soennichsen et al., Biochemistry 31: 8791 (1992)). Accordingly, helical propensity analysis using TFE was performed. Briefly, tested peptides were diluted to 0.2 mg/mL in PBS (pH 7.5) containing 0, 1, 5, 15, 33 or 50% TFE. CD spectra were collected and CD plots were generated after data averaging, buffer subtraction and curve smoothing. Helical propensity values were obtained from mean residue ellipticity (MRE) at 222 nm versus % TFE plots. The concentration of TFE that effected a 50% transformation of the CD spectrum at 222 nm was used as a measure of helical propensity.

The results showed that GLP-2 and GLP-2(A2G) displayed greater helical propensity, requiring ~16% TFE for transformation to maximum helix signal. In comparison, GLP-1 had lower helical propensity, requiring >20% TFE for helical transformation. Significantly, the analog peptides GLP-2(A2G, L17Q) and GLP-2(A2G, N16G, L17Q) both require >20% TFE for helical transformation, bearing a closer resemblance to GLP-1 than to GLP-2. Therefore, L17Q substitution decreased the helix-forming potential of the GLP-2 peptide.

EXAMPLE 8

Mutations in GLP-2 Prevent Mimetibody Dimerization

Nucleic acid sequences encoding GLP-2 mimetibodies with A2G, L17Q (SEQ ID NO: 75) and A2G, N16G, L17Q (SEQ ID NO: 77) analogs were generated using the Quick-Change XL kit from Stratagene. These mimetibody variants were transiently expressed in HEK 293E cells and purified following procedures described in Example 1.

Based on SEC-SLS analysis, GLP-2(A2G, N16G, L17Q) mimetibody exhibited molecular weight consistent with monomer while GLP-2(A2G, L17Q) mimetibody exhibited molecular weight reflective of a monomer and dimer mixture.

EXAMPLE 9

In Vitro Activity of GLP-2 Analog Mimetibodies

The in vitro activity of GLP-2 analogs was tested in a cAMP expression assay. This assay was based on the cAMP Direct screen system from Applied Biosystems utilizing a cell line expressing mutated huGLP-2R in HEK 293E cells. Peptide at concentrations ranging from 0.01 nM to 1.0 uM in PBS with 0.5% BSA was added to ~50,000 cells suspended in 96-well plates. After a 30-minute incubation at 37° C., Lysis Buffer followed by luminescence reagents (Applied Biosystems) was added according to the manufacturers' procedures (Applied Biosystems Luminescence protocol: cAMP-Screen Direct System). Luminescence was quantitated using a Top-Count liquid scintillation analyzer (PerkinElmer), and data was processed using Softmax software (Molecular Devices Corporation). The EC-50 values obtained from plots of cAMP levels versus peptide concentration are listed in Table 5 below.

TABLE 5

EC-50 values of GLP-2 peptides obtained from plots of cAMP versus peptide concentration.

| Structures | Wt-GLP-2 | GLP-2$_{(A2G)}$ | GLP-2$_{(A2G, N16G, L17Q)}$ | GLP-2$_{(A2G, L17Q)}$ |
|---|---|---|---|---|
| cAMP in Vitro EC50 values (nM) | 1.6 | 1.9 | 3.5 | 5.2 |

The data indicate only 2×- and 3×-less activity of GLP-2$_{(A2G, N16G, L17Q)}$ and GLP-2$_{(A2G, L17Q)}$, respectively, relative to wild type GLP-2.

EXAMPLE 10

A2G-GLP-2 Peptide Accelerates Upper GI Transit

To test the effects of A2G-GLP-2 on upper gastrointestinal transit in normal mice, mice were randomly assigned to 2 groups (14 animals per test group). Each group received daily subcutaneous injection (total volume 200 ml) of either A2G-GLP-2 peptide (50 μg/mouse) or the phosphate-buffered saline vehicle for 10 consecutive days.

Figure 3:
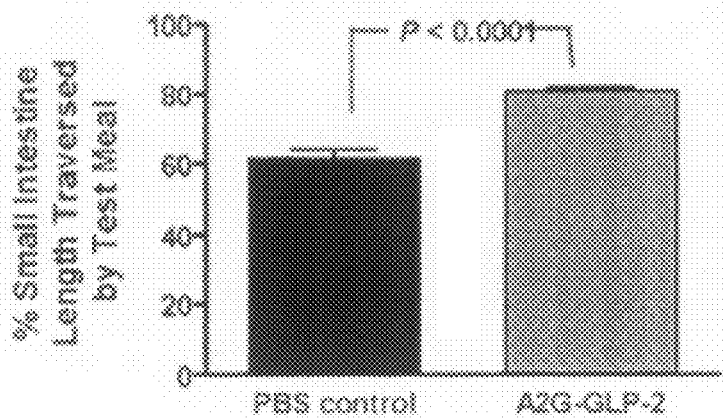
FIG. 3 shows a significant acceleration of intestinal transit in mice treated with A2G-GLP-2 peptide. Statistical significance determined by unpaired Student's T-test.

On the day of study, upper gastrointestinal transit was measured using the carmine dye technique. Mice were fed a test meal of 0.25 ml of a 6% (w/v) solution of carmine cochineal powder mixed into 0.5% (w/v) methylcellulose administered intragastrically by an 18 gauge curved feeding tube. Following oral test meal administration, mice were replaced into their home cages. Twenty minutes after marker meal administration, mice were rapidly euthanized by cervical dislocation and the entire gastrointestinal tract was excised starting from the distal colon and working towards the gastric pylorus. The resected gut was arranged lengthwise parallel to a linear metric scale ruler taking care to avoid stretching the organ. The linear distance traversed by the carmine dye front through the small intestine was measured together with the total length of the small bowel. Upper gastrointestinal transit was expressed as the percentage of the entire small intestine traversed by the carmine dye front during the 20-minute test period; % small intestine traveled= [distance traversed by dye front through small intestine (cm)/ entire small intestine length (cm)×100]. As shown in FIG. 3, A2G-GLP-2 treatment led to an acceleration of upper gastrointestinal transit.

EXAMPLE 11

GLP-2 Mimetibody Accelerates Upper GI Transit

To test the effects of GLP-2 mimetibody on upper gastrointestinal transit in normal mice, mice were randomly assigned to 2 groups (4 animals per group). Each group received a single injection of A2G GLP-2 mimetibody (SEQ ID NO: 5) (4 mg/kg) or the IgG4 negative control 4 days prior to measurement of gastrointestinal transit.

Figure 4:
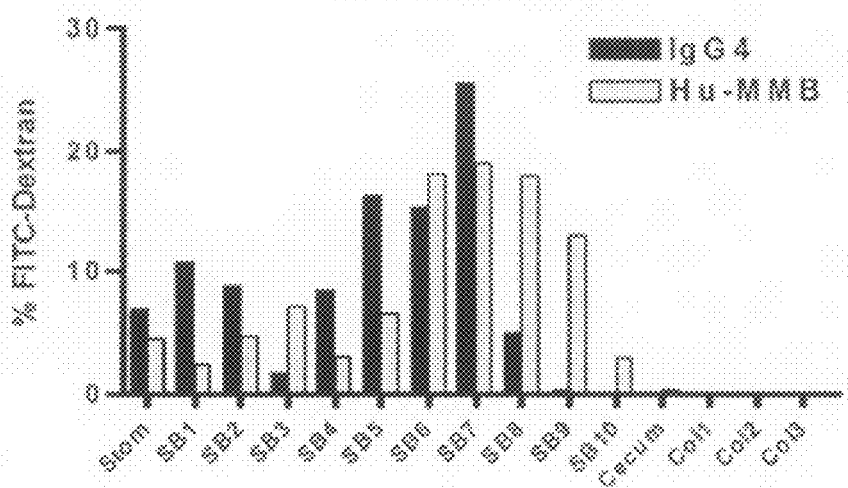
FIG. 4 shows a significant acceleration of intestinal transit in mice treated with A2G GLP-2 mimetibody. Statistical significance determined by unpaired Student's t-test.
Figure 4:
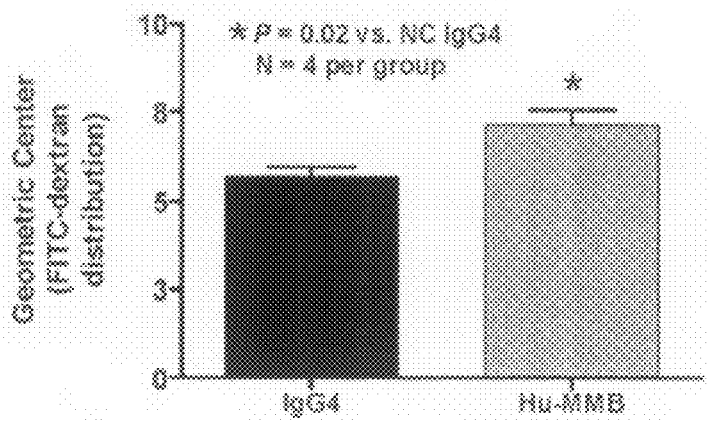

On the day of study, upper gastrointestinal transit was measured using the FITC-dextran method. This method provides both, a measure of gastrointestinal transit and a readout of the pattern of distribution of the test meal along the gastrointestinal tract. Mice were fed a test meal of 150 ml of FITC-dextran solution (5 mg/ml of 70,000 molecular weight dextran conjugated to fluorescein-isothiocyanate in 0.5% methylcellulose/deionized water) administered intragastrically by an 18 gauge curved feeding tube. Following oral administration of the FITC-dextran test meal, mice were returned to their home cages. It was shown that a 30 min test period was the optimum duration for detecting accelerated transit, while a 45 min test period was optimum for detecting delayed transit. Following the appropriate test period, mice were sacrificed by carbon dioxide exposure. The entire gastrointestinal tract from the lower esophageal sphincter to the terminal colon was removed. The bowel segments were opened along the mesenteric border. The tissue and luminal contents of the stomach, 10 equal segments of small intestine, the cecum, and 3 equal segments of colon were placed in individual Eppendorf tubes containing 1 ml of PBS. The tissue was vigorously mixed on a table-top vortex, and solid materials were pelleted by centrifugation. Aliquots of the cleared supernatant were read in duplicate on a 96-well fluorescence plate reader to quantify the magnitude of the fluorescent signal in each segment of bowel. These values were used to calculate the Geometric Center (GC), which is defined as the weighted average distribution of the fluorescent signal along the gastrointestinal tract: GC=Σ(% of total fluorescent signal per segment×segment number)/100. Higher values represent faster rates of transit on scale of 1 to 15. As shown in FIG. 4, one single does of GLP-2 mimetibody treatment led to an acceleration of upper gastrointestinal transit. The mimetibody-induced shift in the distribution pattern of FITC-dextran is shown in the upper panel. There is reduced labeling in the stomach, and an overall shift of the bulk of the label to more distal segments of the small bowel. The GC is calculated in the lower panel for statistical comparison. Normal mice exhibit a GC=6 following a 30 minute test duration, and this was unchanged by treatment with IgG4 scaffold. Treatment with the GLP-2 mimetibody increased the GC to 7.5.

EXAMPLE 12

GLP-2 Mimetibody Attenuates Impaired GI Motility Associated with Post-Operative Inflammatory Ileus Due to immunogenicity of human IgG4 in mice, a murine GLP-2 mimetibody, i.e., human A2G-GLP2 peptide in murine IgG2a scaffold (SEQ ID NO: 80) was used in the following experiments.

To test the effects of GLP-2 mimetibody on impaired GI motility associated with post-operative inflammatory ileus, mice were randomized into 3 groups (8 animals per group) and treated with 2 mg/kg murine A2G-GLP-2 mimetibody, IgG2a or PBS. One hour later, the mice were subject to laparotomy and manipulation of the small intestine. Briefly, male CD-1 mice were anesthetized by inhaled isoflurane and prepared for surgery. The abdomen was shaved of hair and treated with antiseptic solution. The animal was then covered with a surgical drape. The abdomen was opened via mid-line laparotomy, and the entire small intestine was exteriorized onto the sterile drape. Using two moistened, sterile, cotton-tipped applicators, the small intestine was then gently compressed along its length from the ligament of Treitz to the ileo-cecal junction. The small intestine was then returned to the abdominal cavity and the incision sutured closed. Afterwards, the mice were returned to their home cages. A fourth group of 8 animals served as naïve controls.

Figure 5:
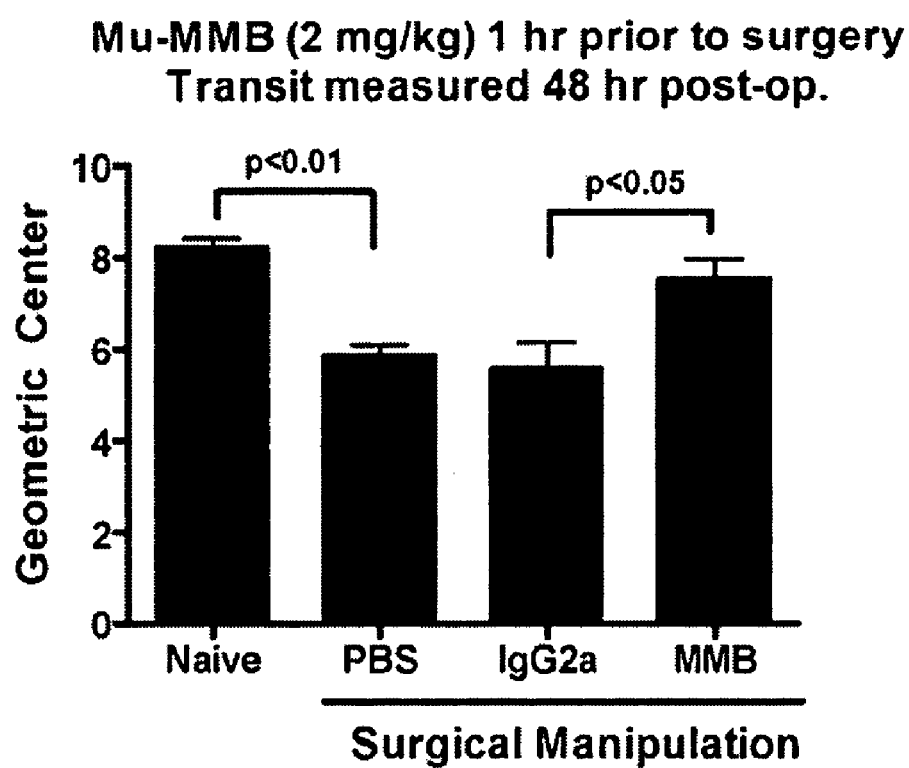
FIG. 5 shows significant attenuation of the delay in gastrointestinal transit associated with post-operative inflammatory ileus in mice treated with murine A2G GLP-2 mimetibody. Statistical significance determined by ANOVA followed by Bonferroni post hoc test.

All mice received an oral test meal of FITC-dextran 48 hr after the operation. Gastrointestinal transit was determined 45 minutes after oral feeding. As shown in FIG. 5, naïve controls exhibited a normal 45-minute transit (GC=8.2). Abdominal surgery led to a significant delay in gastrointestinal transit in PBS-treated animals. Treatment with IgG2a had no effect on the surgically induced delay in transit, whereas treatment with murine A2G-GLP-2 mimetibody led to a significant improvement in transit.

EXAMPLE 13

GLP-2 Mimetibody Reduces Cellular Inflammation Associated with Post-Operative Inflammatory Ileus To test the effects of GLP-2 mimetibody on cellular inflammation, post-operative inflammatory ileus was induced in mice as described in Example 12. Myeloperoxidase histochemistry was performed on tissues harvested from the mid-small bowel of the mice 48 hr after the operation.

Briefly, segments of mid-small bowel were collected from the centrifuge tubes described in Example 12. Whole mounts of the muscle layer were prepared by pinning the tissue flat in a Sylgard® lined Petri dish and stretching the tissue to 2 times its length and 1.5 times its width. The mucosa was removed by fine dissection. The muscularis whole mounts were then fixed with 100% ethanol for 1 hr, washed 3 times with PBS, and incubated for 20 min in PBS containing 0.1% hydrogen peroxide and 1 mg/ml Hanker-Yates reagent. Following a second wash with PBS, the whole mounts were mounted on glass slides, cover-slipped, and viewed on an optical microscope. Myeloperoxidase containing leukocytes were counted in 6 to 8 adjacent 200× optical fields of view and the mean cell counts were calculated and recorded.

Figure 6:
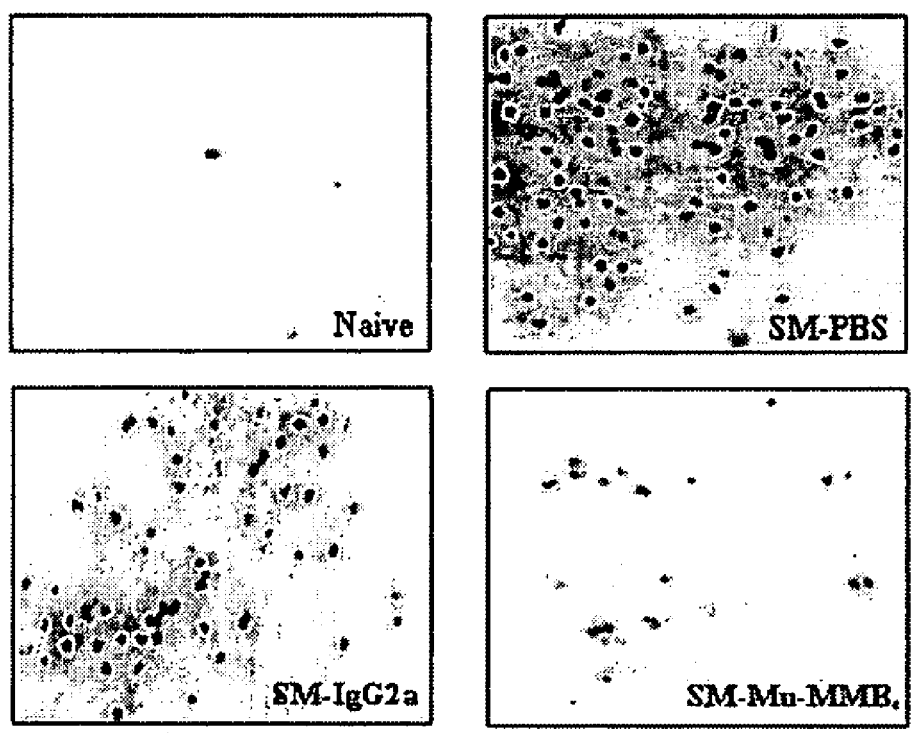
FIG. 6 shows the whole mounts of intestinal muscularis with increased numbers of myeloperoxidase (MPO)-containing leukocytes following abdominal surgery. Treatment with murine A2G GLP-2 mimetibody significantly reduced the number of infiltrating cells, whereas IgG2a had no effect.
Figure 7:
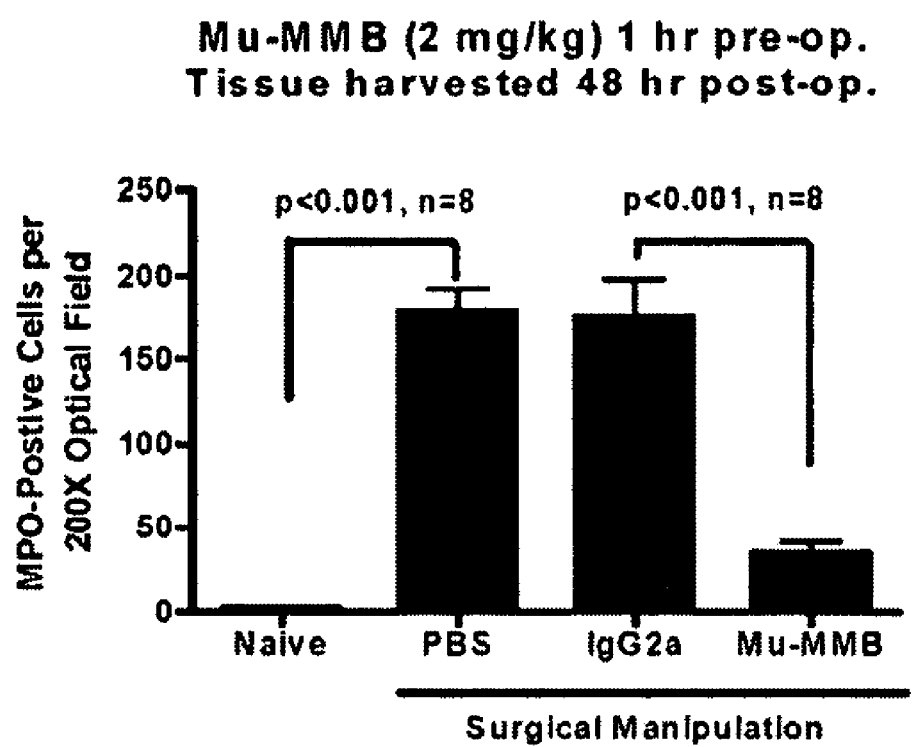
FIG. 7 shows the histogram with compiled cell counts from FIG. 6. Statistical significance determined by ANOVA followed by Bonferroni post hoc test.

Representative whole mounts of intestinal muscularis stained for myeloperoxidase (MPO) activity using Hanker-Yates reagent are shown in FIG. 6. Black dots represent MPO-positive leukocytes infiltrating the small intestinal muscle layer. Few MPO-positive cells were found in tissue harvested from naïve mice. A marked increase in the number of infiltrating leukocytes was found in mice treated with PBS prior to undergoing surgical manipulation of the small bowel. Treatment with IgG2a had no effect on the numbers of infiltrating cells. In contrast, treatment with murine A2G-GLP-2 mimetibody significantly reduced the number of infiltrating cells. Cell counts are compiled in FIG. 7 for statistical comparison.

The present invention now being fully described, it will be apparent to one of ordinary skill in the art that many changes and modifications can be made thereto without departing from the spirit or scope of the appended claims.

The invention claimed is:

1. A polypeptide comprising the amino acid sequence shown in SEQ ID NO: 55.

2. A pharmaceutical composition comprising the polypeptide according to claim 1 and a pharmaceutically acceptable carrier or diluent.

3. A mimetibody that binds to human GLP-2 receptor according to formula (II):

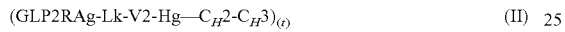
$$(\text{GLP2RAg-Lk-V2-Hg}—C_H2-C_H3)_{(t)} \quad (\text{II})$$

where GLP2RAg is a human GLP-2R agonist comprising the amino acid sequence shown in SEQ ID NO:55, Lk is a polypeptide or chemical linkage, V2 is a portion of a C-terminus of an immunoglobulin variable region, Hg is at least a portion of an immunoglobulin variable hinge region, $C_H2$ is an immunoglobulin heavy chain $C_H2$ constant region and $C_H3$ is an immunoglobulin heavy chain $C_H3$ constant region and t is independently an integer from 1 to 10.

4. The mimetibody of claim 3 wherein Hg, $C_H2$ and $C_H3$ are of the IgG1 subclass.

5. The mimetibody of claim 4 wherein comprises the amino acid sequence shown in SEQ ID NO:24 and $C_H2$ comprises the amino acid sequence shown in SEQ ID NO:29.

6. The mimetibody of claim 3 wherein Hg is of the IgG4 subclass, and $C_H2$ and $C_H3$ are of the IgG1 subclass.

7. The mimetibody of claim 3 wherein Hg, $C_H2$ and $C_H3$ are of the IgG4 subclass.

8. The mimetibody of claim 7 wherein Hg comprises the amino acid sequence shown in SEQ ID NO:26 and $C_H2$ comprises the amino acid sequence shown in SEQ ID NO:31.

9. A mimetibody according to claim 3 comprising the amino acid sequence shown in SEQ ID NO:63 or SEQ ID NO:77.

10. A pharmaceutical composition comprising at least one mimetibody according to any one of claim 3, 4, 5, 6, 7, 8 or 9 and a pharmaceutically acceptable carrier or diluent.

* * * * *